(12) United States Patent
Stupecky et al.

(10) Patent No.: US 10,835,720 B2
(45) Date of Patent: *Nov. 17, 2020

(54) METHODS FOR MANUFACTURING MULTI-LAYER BALLOONS FOR MEDICAL APPLICATIONS

(71) Applicant: Confluent Medical Technologies, Inc., Fremont, CA (US)

(72) Inventors: Josef J. Stupecky, Laguna Niguel, CA (US); Eric Mabry, Trabuco Canyon, CA (US)

(73) Assignee: CONFLUENT MEDICAL TECHNOLOGIES, INC., Fremont, CA (US)

( * ) Notice: Subject to any disclaimer, the term of this patent is extended or adjusted under 35 U.S.C. 154(b) by 298 days.

This patent is subject to a terminal disclaimer.

(21) Appl. No.: 15/701,839

(22) Filed: Sep. 12, 2017

(65) Prior Publication Data

US 2018/0064917 A1  Mar. 8, 2018

Related U.S. Application Data

(60) Continuation of application No. 14/065,243, filed on Oct. 28, 2013, now Pat. No. 9,833,600, which is a
(Continued)

(51) Int. Cl.
*A61M 25/10* (2013.01)

(52) U.S. Cl.
CPC ........ *A61M 25/1036* (2013.01); *A61M 25/10* (2013.01); *A61M 2025/1004* (2013.01);
(Continued)

(58) Field of Classification Search
None
See application file for complete search history.

(56) References Cited

U.S. PATENT DOCUMENTS

| 1,051,777 A | 1/1913 | Mars |
| 1,210,895 A | 1/1917 | Brinkman |
| (Continued) | | |

FOREIGN PATENT DOCUMENTS

| BE | 863490 | 2/1978 |
| CA | 2043346 | 11/1992 |
| (Continued) | | |

OTHER PUBLICATIONS

U.S. Appl. No. 14/924,278, filed Oct. 27, 2015, Stupecky et al.
(Continued)

*Primary Examiner* — Monica A Huson
(74) *Attorney, Agent, or Firm* — Knobbe, Martens, Olson & Bear, LLP

(57) ABSTRACT

A multi-layered balloon is provided where each layer is formed such that each layer is made from tubing that optimizes the inner wall stretch thus providing maximum balloon strength. The high pressure, multi-layer balloon is provided with layers that allow for slipping, such that the balloon has a very high pressure rating and toughness, yet excellent folding characteristics. Methods for producing such multi-layer balloons using existing balloon forming equipment are also provided. The multi-layer balloons can have alternating structural and lubricating layers, or layers with low-friction surfaces. The multi-layer balloons are preferably manufactured using a variety of methods including nesting, co-extrusion, or a combination of nesting and co-extrusion. The multi-layer balloons have balloon layers having substantially similar, or the same, high degree of biaxial orientation of their polymer molecules such that each balloon layer of the multi-layer balloon will fail at approximately the same applied pressure.

20 Claims, 22 Drawing Sheets

Related U.S. Application Data continuation of application No. 13/108,868, filed on May 16, 2011, now Pat. No. 8,568,648, which is a division of application No. 11/611,748, filed on Dec. 15, 2006, now Pat. No. 7,942,847.

(60) Provisional application No. 60/751,014, filed on Dec. 16, 2005, provisional application No. 60/831,529, filed on Jul. 18, 2006.

(52) U.S. Cl.
CPC .. *A61M 2025/1075* (2013.01); *Y10T 156/101* (2015.01); *Y10T 428/1317* (2015.01)

(56) References Cited

U.S. PATENT DOCUMENTS

| | | |
|---|---|---|
| 1,894,800 A | 1/1933 | Stowe |
| 2,030,803 A | 2/1936 | Temple |
| 2,617,319 A | 11/1952 | Richards |
| 3,044,326 A | 7/1962 | Erich |
| 3,273,367 A | 9/1966 | Hallden |
| 3,374,651 A | 3/1968 | Haug |
| 3,587,287 A | 6/1971 | Vacca |
| 3,645,126 A | 2/1972 | Kralowetz et al. |
| 3,648,501 A | 3/1972 | Kralowetz |
| 3,668,915 A | 6/1972 | Ribback |
| 3,845,650 A | 11/1974 | Romanov |
| 4,047,420 A | 9/1977 | Edwards |
| 4,327,736 A | 5/1982 | Inoue |
| 4,384,470 A | 5/1983 | Fiore |
| 4,418,458 A | 12/1983 | Hunter |
| 4,637,396 A | 1/1987 | Cook |
| 4,651,721 A | 3/1987 | Mikulich et al. |
| 4,651,738 A | 3/1987 | Demer |
| 4,685,447 A | 8/1987 | Iversen et al. |
| 4,696,085 A | 9/1987 | Sauder |
| 4,702,252 A | 10/1987 | Brooks et al. |
| 4,781,192 A | 11/1988 | Demer |
| 4,891,877 A | 1/1990 | Talavera |
| 4,932,956 A | 6/1990 | Reddy et al. |
| 4,932,958 A | 6/1990 | Reddy et al. |
| 5,105,091 A | 4/1992 | Igarashi |
| 5,142,160 A | 8/1992 | Storbeck |
| 5,171,299 A | 12/1992 | Heitzmann et al. |
| 5,184,733 A | 2/1993 | Arnarson et al. |
| 5,195,969 A | 3/1993 | Wang et al. |
| 5,201,706 A | 4/1993 | Noguchi et al. |
| 5,207,700 A | 5/1993 | Euteneuer |
| 5,270,086 A | 12/1993 | Hamlin |
| 5,290,306 A | 3/1994 | Trotta et al. |
| 5,304,340 A | 4/1994 | Downey |
| 5,342,305 A | 8/1994 | Shonk |
| 5,344,400 A | 9/1994 | Kaneko et al. |
| 5,344,401 A | 9/1994 | Radisch et al. |
| 5,350,361 A | 9/1994 | Tsukashima et al. |
| 5,358,486 A | 10/1994 | Saab |
| 5,358,487 A | 10/1994 | Miller |
| 5,366,442 A | 11/1994 | Wang et al. |
| 5,445,646 A | 8/1995 | Euteneuer et al. |
| 5,447,497 A | 9/1995 | Sogard et al. |
| 5,478,320 A | 12/1995 | Trotta |
| 5,499,980 A | 3/1996 | Euteneuer |
| 5,500,180 A | 3/1996 | Bard |
| 5,512,051 A | 4/1996 | Wang et al. |
| 5,514,092 A | 5/1996 | Forman et al. |
| 5,538,510 A | 7/1996 | Fontirroche et al. |
| 5,587,125 A | 12/1996 | Roychowdhury |
| 5,609,056 A | 3/1997 | Seeber |
| 5,613,979 A | 3/1997 | Trotta et al. |
| 5,620,649 A | 4/1997 | Trotta |
| 5,647,848 A | 7/1997 | Jorgensen |
| 5,681,522 A | 10/1997 | Roychowdhury |
| 5,693,014 A | 12/1997 | Abele et al. |
| 5,746,745 A | 5/1998 | Abele et al. |
| 5,752,934 A | 5/1998 | Campbell et al. |
| 5,755,690 A | 5/1998 | Saab |
| 5,797,877 A | 8/1998 | Hamilton et al. |
| 5,807,327 A | 9/1998 | Green et al. |
| 5,820,594 A | 10/1998 | Fontirroche et al. |
| 5,833,657 A | 11/1998 | Reinhardt et al. |
| 5,841,541 A | 11/1998 | Dlugos |
| 5,843,027 A | 12/1998 | Stone et al. |
| 5,865,721 A | 2/1999 | Andrews et al. |
| 5,868,704 A | 2/1999 | Campbell et al. |
| 5,868,776 A | 2/1999 | Wright |
| 5,879,282 A | 3/1999 | Fischell et al. |
| 5,879,369 A | 3/1999 | Ishida |
| 5,908,406 A | 6/1999 | Ostapchenko et al. |
| 5,947,993 A | 9/1999 | Morales |
| 5,960,379 A | 9/1999 | Shimizu et al. |
| 6,004,289 A | 12/1999 | Saab |
| 6,010,480 A | 1/2000 | Abele et al. |
| 6,024,722 A | 2/2000 | Rau et al. |
| 6,024,752 A | 2/2000 | Horn et al. |
| 6,036,697 A | 3/2000 | DiCaprio |
| 6,059,751 A | 5/2000 | Ostapchenko et al. |
| 6,070,446 A | 6/2000 | Blaimschein |
| 6,086,556 A | 7/2000 | Hamilton et al. |
| 6,120,477 A | 9/2000 | Campbell et al. |
| 6,124,007 A | 9/2000 | Wang et al. |
| 6,132,824 A | 10/2000 | Hamlin |
| 6,136,011 A | 10/2000 | Stambaugh |
| 6,136,258 A | 10/2000 | Wang et al. |
| 6,141,106 A | 10/2000 | Blum |
| 6,242,063 B1 | 6/2001 | Ferrera et al. |
| 6,293,959 B1 | 9/2001 | Miller et al. |
| 6,296,633 B1 | 10/2001 | Helgerson |
| 6,308,546 B1 | 10/2001 | Blaimschein et al. |
| 6,319,228 B1 | 11/2001 | Kastenhofer |
| 6,328,925 B1 | 12/2001 | Wang et al. |
| 6,358,227 B1 | 3/2002 | Ferrera et al. |
| 6,360,577 B2 | 3/2002 | Austin |
| 6,395,208 B1 | 5/2002 | Herweck et al. |
| 6,419,685 B2 | 7/2002 | Di Caprio et al. |
| 6,453,729 B1 | 9/2002 | Muto et al. |
| 6,461,326 B1 | 10/2002 | Yang et al. |
| 6,481,262 B2 | 11/2002 | Ching et al. |
| 6,482,348 B1 | 11/2002 | Wang et al. |
| 6,506,202 B1 | 1/2003 | Dutta et al. |
| 6,517,547 B1 | 2/2003 | Feeser et al. |
| 6,547,768 B2 | 4/2003 | Trotta |
| 6,585,688 B2 | 7/2003 | Ferrera et al. |
| 6,645,422 B2 | 11/2003 | Jung et al. |
| 6,695,809 B1 | 2/2004 | Lee |
| 6,701,633 B2 | 3/2004 | Ohtsuka |
| 6,756,094 B1 | 6/2004 | Wang et al. |
| 6,773,447 B2 | 8/2004 | Laguna |
| 6,787,095 B2 | 9/2004 | Wang et al. |
| 6,866,649 B2 | 3/2005 | Ferrera et al. |
| 6,872,215 B2 | 3/2005 | Crocker et al. |
| 6,881,216 B2 | 4/2005 | Di Caprio et al. |
| 6,896,842 B1 | 5/2005 | Hamilton et al. |
| 6,902,571 B2 | 6/2005 | Owens et al. |
| 6,911,017 B2 | 6/2005 | Lee et al. |
| 6,923,787 B2 | 8/2005 | Wang |
| 6,946,173 B2 | 9/2005 | Lim et al. |
| 6,951,675 B2 | 10/2005 | Chin et al. |
| 6,955,661 B1 | 10/2005 | Herweck et al. |
| 6,972,024 B1 | 12/2005 | Kilpatrick et al. |
| 6,988,881 B2 | 1/2006 | Motsenbocker et al. |
| 6,993,953 B2 | 2/2006 | Stupecky |
| 7,010,953 B2 | 3/2006 | Stupecky |
| 7,025,745 B2 | 4/2006 | Lim et al. |
| 7,026,026 B2 | 4/2006 | Ferrera et al. |
| 7,037,562 B2 | 5/2006 | Jimenez |
| 7,105,013 B2 | 9/2006 | Durcan |
| 7,108,684 B2 | 9/2006 | Farnan |
| 7,126,694 B1 | 10/2006 | Bachalo |
| 7,147,905 B2 | 12/2006 | Fukuda et al. |
| 7,172,796 B2 | 2/2007 | Kinoshita et al. |
| 7,290,352 B2 | 11/2007 | Defarne et al. |
| 7,314,461 B2 | 1/2008 | Carter et al. |
| 7,314,480 B2 | 1/2008 | Eidenschink et al. |

(56) References Cited

U.S. PATENT DOCUMENTS

| | | |
|---|---|---|
| 7,335,184 B2 | 2/2008 | Laguna |
| 7,367,989 B2 | 5/2008 | Eidenschink |
| 7,389,670 B1 | 6/2008 | Kokish et al. |
| 7,418,851 B2 | 9/2008 | Labro |
| 7,448,243 B1 | 11/2008 | Motsenbocker |
| 7,449,010 B1 | 11/2008 | Hayase et al. |
| 7,553,292 B2 | 6/2009 | Kilpatrick et al. |
| 7,578,165 B1 | 8/2009 | Stupecky |
| 7,637,886 B2 | 12/2009 | Herweck et al. |
| 7,641,688 B2 | 1/2010 | Lesh |
| 7,659,000 B2 | 2/2010 | Burgmeier et al. |
| 7,670,364 B2 | 3/2010 | Dusbabek et al. |
| 7,682,335 B2 | 3/2010 | Pepper et al. |
| 7,682,553 B2 | 3/2010 | Wang et al. |
| 7,713,233 B2 | 5/2010 | Burgmeier et al. |
| 7,713,281 B2 | 5/2010 | Leeflang et al. |
| 7,731,685 B2 | 6/2010 | Ragheb et al. |
| 7,758,572 B2 | 7/2010 | Weber et al. |
| 7,762,804 B1 | 7/2010 | Stupecky |
| 7,762,984 B2 | 7/2010 | Kumoyama et al. |
| 7,781,038 B2 | 8/2010 | Hamilton et al. |
| 7,828,766 B2 | 11/2010 | Durcan |
| 7,914,486 B2 | 3/2011 | Chen et al. |
| 7,942,847 B2 | 5/2011 | Stupecky et al. |
| 7,947,059 B2 | 5/2011 | Chin et al. |
| 7,951,110 B2 | 5/2011 | Bishop et al. |
| 7,976,497 B2 | 7/2011 | Shah et al. |
| 7,985,228 B2 | 7/2011 | Phan et al. |
| 7,985,234 B2 | 7/2011 | Wang et al. |
| 8,002,744 B2 | 8/2011 | Pepper et al. |
| 8,025,943 B2 | 9/2011 | Hamilton et al. |
| 8,034,066 B2 | 10/2011 | Goeken et al. |
| 8,043,296 B2 | 10/2011 | Chasmawala et al. |
| 8,043,362 B2 | 10/2011 | Gong et al. |
| 8,048,028 B2 | 11/2011 | Horn et al. |
| 8,052,638 B2 | 11/2011 | Lee et al. |
| 8,066,780 B2 | 11/2011 | Chen et al. |
| 8,070,719 B2 | 12/2011 | Lee |
| 8,122,809 B2 | 2/2012 | Simpson |
| 8,162,969 B2 | 4/2012 | Brister et al. |
| 8,257,074 B1 | 9/2012 | Stupecky |
| 8,388,575 B2 | 3/2013 | Durcan |
| 8,394,055 B2 | 3/2013 | Durcan |
| 8,440,090 B2 | 5/2013 | Haslinger et al. |
| 8,444,608 B2 | 5/2013 | Haslinger et al. |
| 8,535,596 B2 | 9/2013 | Durcan |
| 8,568,648 B2 | 10/2013 | Stupecky et al. |
| 8,684,963 B2 | 4/2014 | Qiu et al. |
| 8,752,261 B2 | 6/2014 | Van Sciver |
| 8,864,786 B2 | 10/2014 | Deshmukh |
| 9,089,669 B2 | 7/2015 | Haslinger et al. |
| 9,095,689 B2 | 8/2015 | Durcan |
| 9,211,392 B2 | 12/2015 | Durcan |
| 9,265,918 B2 | 2/2016 | Chen et al. |
| 9,381,325 B2 | 7/2016 | Haslinger et al. |
| 9,625,069 B2 | 4/2017 | Schwager |
| 9,833,600 B2 * | 12/2017 | Stupecky ............... A61M 25/10 |
| 2001/0001890 A1 | 5/2001 | Austin |
| 2002/0018866 A1 | 2/2002 | Lee et al. |
| 2002/0090476 A1 | 7/2002 | Ling et al. |
| 2002/0122903 A1 | 9/2002 | Ferrera et al. |
| 2002/0163104 A1 | 11/2002 | Motsenbocker et al. |
| 2002/0165523 A1 | 11/2002 | Chin et al. |
| 2002/0177866 A1 | 11/2002 | Weikel et al. |
| 2002/0187289 A1 | 12/2002 | Chang et al. |
| 2003/0093107 A1 | 5/2003 | Parsonage et al. |
| 2003/0149468 A1 | 8/2003 | Wallsten |
| 2004/0006359 A1 | 1/2004 | Laguna |
| 2004/0019362 A1 | 1/2004 | Ferrera et al. |
| 2004/0078052 A1 | 4/2004 | St. Pierre et al. |
| 2004/0096538 A1 | 5/2004 | Goff et al. |
| 2004/0098021 A1 | 5/2004 | Laguna |
| 2004/0181252 A1 | 9/2004 | Boyle et al. |
| 2004/0191443 A1 | 9/2004 | Hamlin |
| 2004/0207127 A1 | 10/2004 | Hamlin |
| 2005/0008560 A1 | 1/2005 | Kataoka et al. |
| 2005/0015047 A1 | 1/2005 | Shah |
| 2005/0015105 A1 | 1/2005 | Tang et al. |
| 2005/0027248 A1 | 2/2005 | Suzuki et al. |
| 2005/0043679 A1 | 2/2005 | Devens, Jr. et al. |
| 2005/0075711 A1 | 4/2005 | Neary |
| 2005/0113856 A1 | 5/2005 | Epstein et al. |
| 2005/0137619 A1 | 6/2005 | Schewe et al. |
| 2005/0209629 A1 | 9/2005 | Kerr et al. |
| 2005/0228429 A1 | 10/2005 | Burgmeier et al. |
| 2005/0231721 A1 | 10/2005 | Lnenaga et al. |
| 2005/0238833 A1 | 10/2005 | Wang et al. |
| 2005/0251107 A1 | 11/2005 | Olson |
| 2005/0261721 A1 | 11/2005 | Radish, Jr. et al. |
| 2005/0261760 A1 | 11/2005 | Weber |
| 2005/0266109 A1 | 12/2005 | Chin et al. |
| 2005/0267596 A1 | 12/2005 | Chen et al. |
| 2005/0288630 A1 | 12/2005 | Conway |
| 2006/0079918 A1 | 4/2006 | Creston |
| 2006/0079922 A1 | 4/2006 | Creston |
| 2006/0085023 A1 | 4/2006 | Davies, Jr. et al. |
| 2006/0165926 A1 | 7/2006 | Weber |
| 2006/0182873 A1 | 8/2006 | Klisch et al. |
| 2007/0055301 A1 | 3/2007 | Campbell et al. |
| 2007/0142772 A1 | 6/2007 | Deshmukh et al. |
| 2007/0167973 A1 | 7/2007 | Stupecky et al. |
| 2008/0051760 A1 | 2/2008 | Schoenle et al. |
| 2008/0065188 A1 | 3/2008 | Pallazza |
| 2008/0086083 A1 | 4/2008 | Towler |
| 2008/0097301 A1 | 4/2008 | Alpini et al. |
| 2008/0125711 A1 | 5/2008 | Alpini et al. |
| 2008/0157444 A1 | 7/2008 | Melsheimer |
| 2008/0228138 A1 | 9/2008 | Van Sloten et al. |
| 2009/0048684 A1 | 2/2009 | Lesh |
| 2009/0089079 A1 | 4/2009 | Goldhaber et al. |
| 2009/0299401 A1 | 12/2009 | Tilson |
| 2009/0299450 A1 | 12/2009 | Johnson et al. |
| 2009/0312806 A1 | 12/2009 | Sherman et al. |
| 2010/0042199 A1 | 2/2010 | Burton |
| 2010/0049123 A1 | 2/2010 | Alpini et al. |
| 2010/0100107 A1 | 4/2010 | Duggal et al. |
| 2010/0145266 A1 | 6/2010 | Orlowski |
| 2010/0174235 A1 | 7/2010 | Yamaguchi |
| 2010/0191089 A1 | 7/2010 | Stebler et al. |
| 2010/0234875 A1 | 9/2010 | Allex et al. |
| 2010/0241152 A1 | 9/2010 | Tilson et al. |
| 2010/0252965 A1 | 10/2010 | Wang et al. |
| 2010/0262218 A1 | 10/2010 | Deshmukh |
| 2010/0331965 A1 | 12/2010 | Dugas et al. |
| 2011/0022150 A1 | 1/2011 | Durcan |
| 2011/0022152 A1 | 1/2011 | Grandt |
| 2011/0046724 A1 | 2/2011 | Heilmann et al. |
| 2011/0160661 A1 | 6/2011 | Elton |
| 2011/0214802 A1 | 9/2011 | Stupecky et al. |
| 2011/0295203 A1 | 12/2011 | Hayes et al. |
| 2012/0016405 A1 | 1/2012 | Hamilton et al. |
| 2012/0065718 A1 | 3/2012 | Simpson et al. |
| 2013/0184643 A1 | 7/2013 | Warnack |
| 2013/0253425 A1 | 9/2013 | Haslinger et al. |
| 2014/0116606 A1 | 5/2014 | Stupecky et al. |
| 2014/0155823 A1 | 6/2014 | Qiu et al. |
| 2014/0276401 A1 | 9/2014 | Lee et al. |
| 2014/0319750 A1 | 10/2014 | Stupecky et al. |
| 2015/0073468 A1 | 3/2015 | Yang |
| 2015/0105815 A1 | 4/2015 | Horn et al. |
| 2015/0320969 A1 | 11/2015 | Haslinger et al. |
| 2015/0367109 A1 | 12/2015 | Maeda et al. |
| 2016/0008589 A1 | 1/2016 | Stupecky et al. |
| 2016/0058981 A1 | 3/2016 | Durcan |
| 2016/0114141 A1 | 4/2016 | Mabry et al. |
| 2016/0129158 A1 | 5/2016 | Chen et al. |

FOREIGN PATENT DOCUMENTS

| | | |
|---|---|---|
| CA | 2199333 | 10/2000 |
| CA | 2775946 | 4/2011 |
| DE | 10125998 | 11/2002 |
| EP | 0421031 | 4/1991 |
| EP | 1611917 | 1/2006 |

(56) References Cited

FOREIGN PATENT DOCUMENTS

| | | |
|---|---|---|
| EP | 1948286 | 8/2017 |
| EP | 2 783 722 | 1/2019 |
| EP | 2 029 215 | 3/2019 |
| JP | 02119874 | 5/1990 |
| JP | H09-507141 | 7/1997 |
| JP | H10-314311 | 12/1998 |
| JP | 2004-512980 | 4/2004 |
| JP | 2009-519770 | 5/2009 |
| JP | 2012-504018 | 2/2012 |
| JP | 6486297 | 3/2019 |
| WO | WO 95/17920 | 7/1995 |
| WO | WO 96/40350 | 12/1996 |
| WO | WO 97/32624 | 9/1997 |
| WO | WO 99/13924 | 3/1999 |
| WO | WO 2001/064278 | 9/2001 |
| WO | WO 2001/089619 | 11/2001 |
| WO | WO 2002/36196 | 5/2002 |
| WO | WO 2003/004248 | 1/2003 |
| WO | WO 2005/115496 | 12/2005 |
| WO | WO 2007/075585 | 7/2007 |
| WO | WO 2009/006748 | 1/2009 |
| WO | WO 2013/145479 | 3/2013 |
| WO | WO 2014/179505 | 11/2014 |
| WO | WO 2016/007928 | 1/2016 |
| WO | WO 2016/069640 | 5/2016 |

OTHER PUBLICATIONS

International Search Report with Written Opinion of the International Searching Authority dated Jul. 2, 2008, for corresponding International Application No. PCT/US06/48268, filed Dec. 15, 2006.

Japanese Office Action dated Dec. 21, 2012 in Japanese Application No. 2008-545887 referencing a Japanese Office Action dated Dec. 6, 2011 (total of 4 pages).

Canadian Office Action dated Jan. 9, 2013 in Canadian Application No. 2,633,578 in 3 pages.

European Office Action for European Application No. 06845731.6-1526, dated Jun. 6, 2012 in 5 pages.

Japanese Office Action for Japanese Application No. 2008-545887, dated Dec. 6, 2011 in 6 pages.

Sample Measurement Testing, in U.S. Appl. No. 11/303,545, filed Nov. 17, 2008.

European Office Action for European Application No. 06845731.6-1526, dated Feb. 16, 2016 in 5 pages.

International Search Report and Written Opinion in PCT/US2014/036259 dated Apr. 30, 2015 in 8 pages.

International Search Report and Written Opinion in PCT/US2015/0040056 dated Jul. 10, 2015 in 10 pages.

International Search Report and Written Opinion in PCT/US2015/057642 dated Oct. 27, 2015 in 10 pages.

OPN NC 35 atm High Pressure Balloon, 4 pages, dated 2012.

Extended European Search Report for European Application No. 15854288, dated Jun. 15, 2018 in 6 pages.

Intention to Grant for European Application No. 06845731.6-1526, dated Jul. 19, 2018 in 7 pages.

Office Action for Japanese Application No. 2017-522970, dated Aug. 9, 2019 in 4 pages.

\* cited by examiner

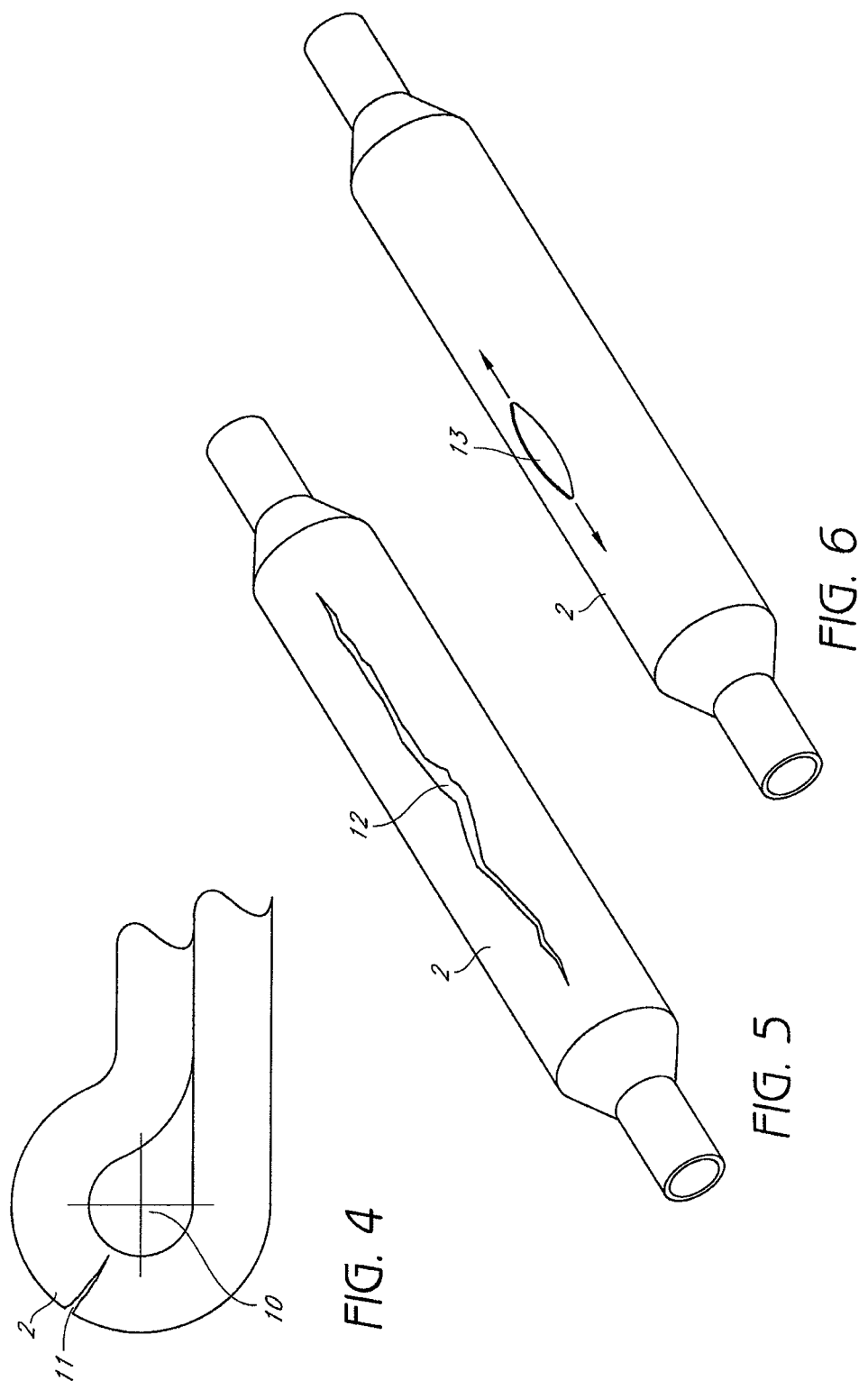

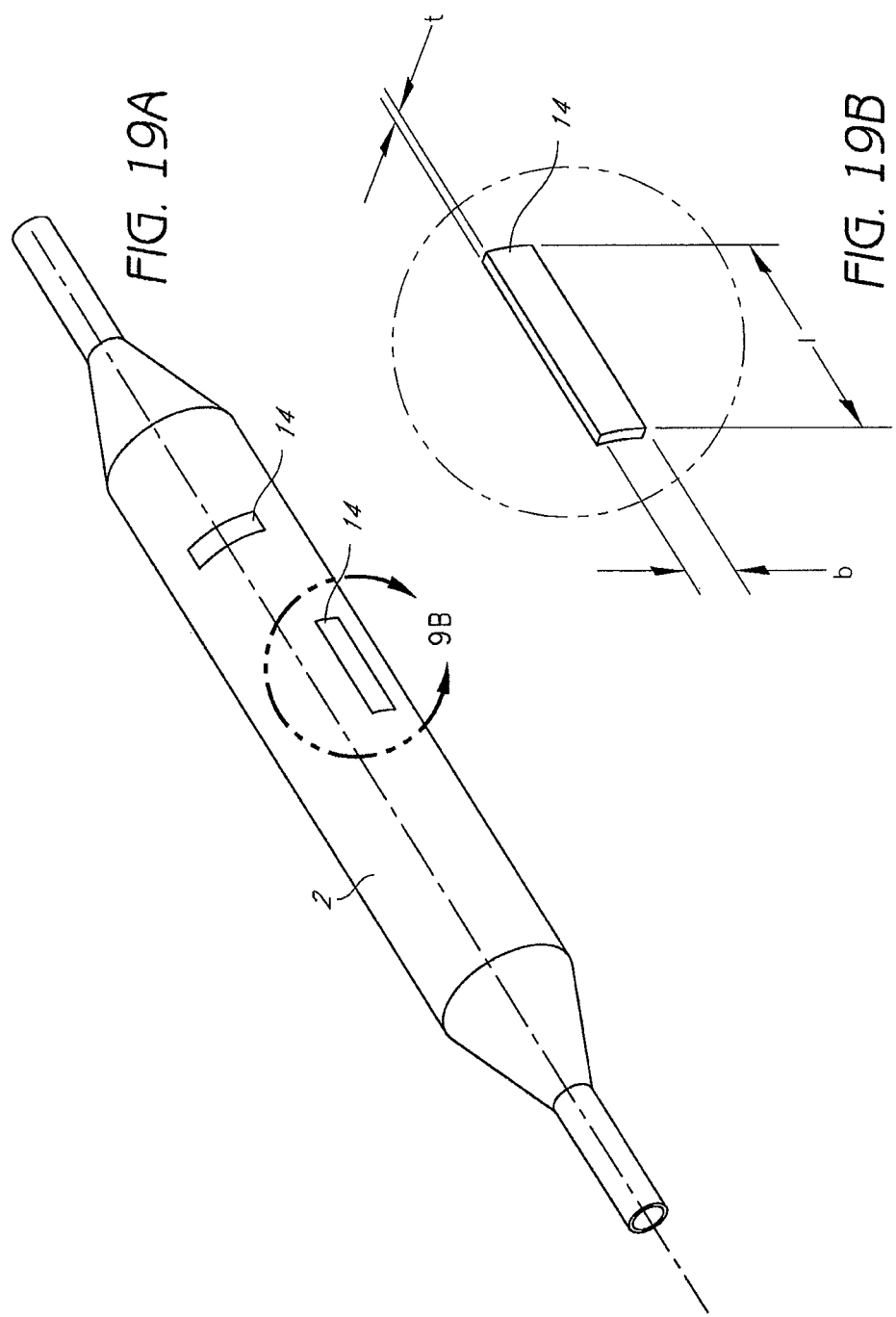

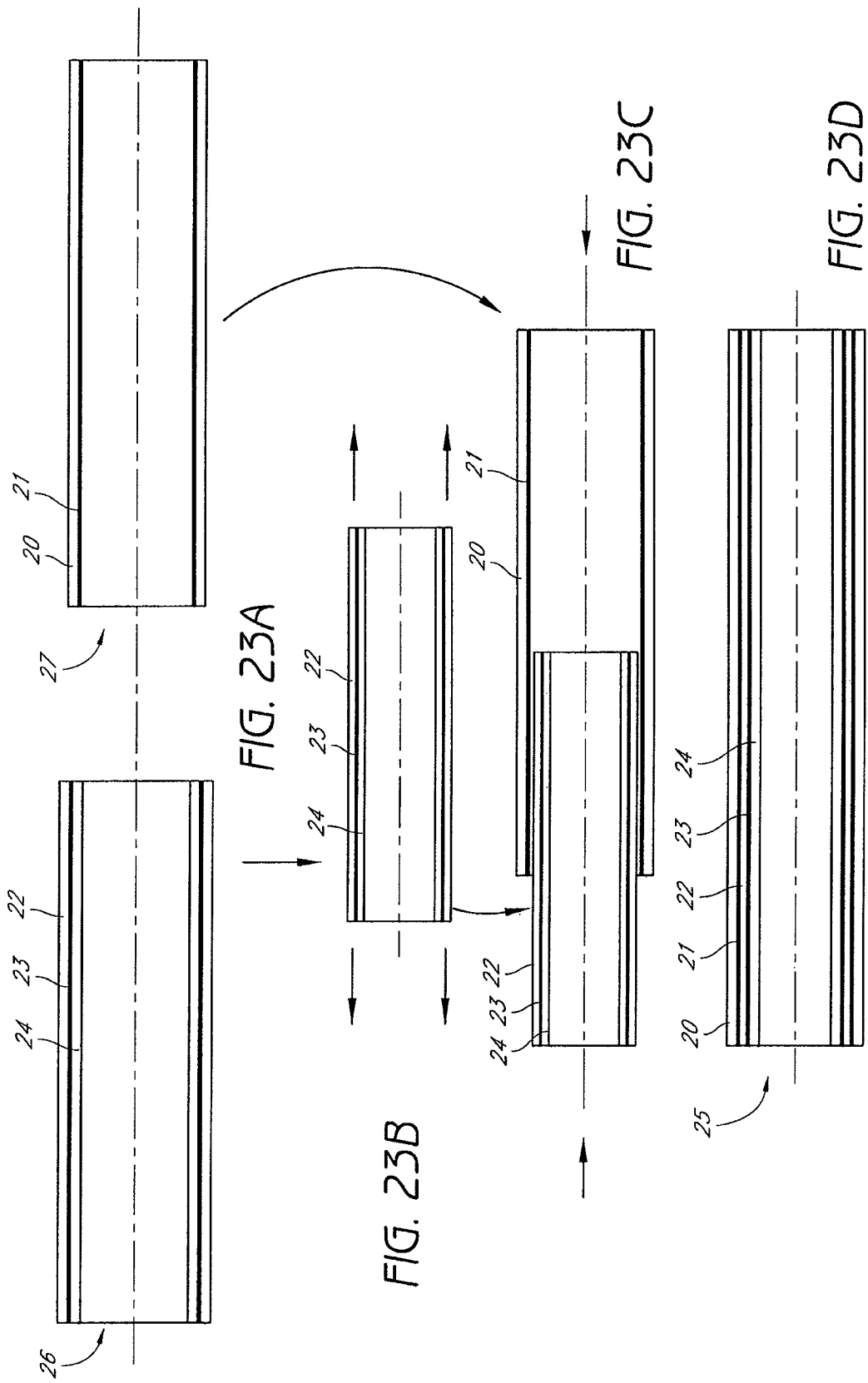

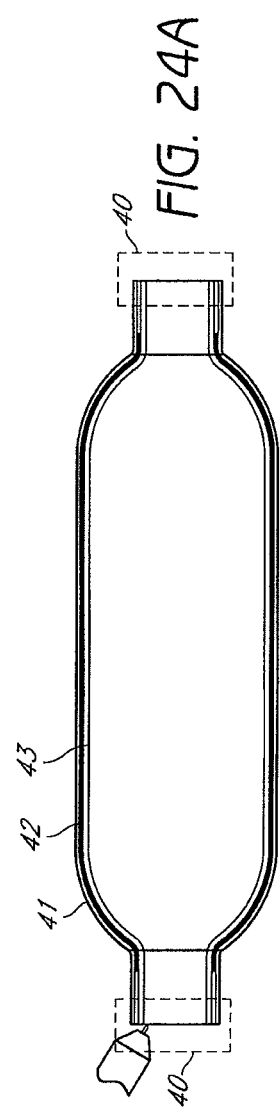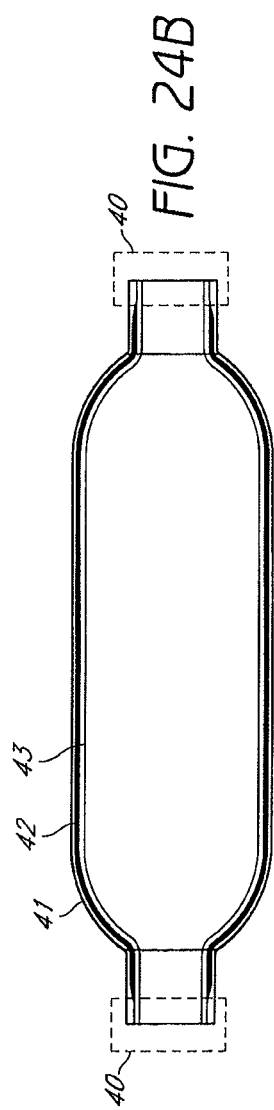

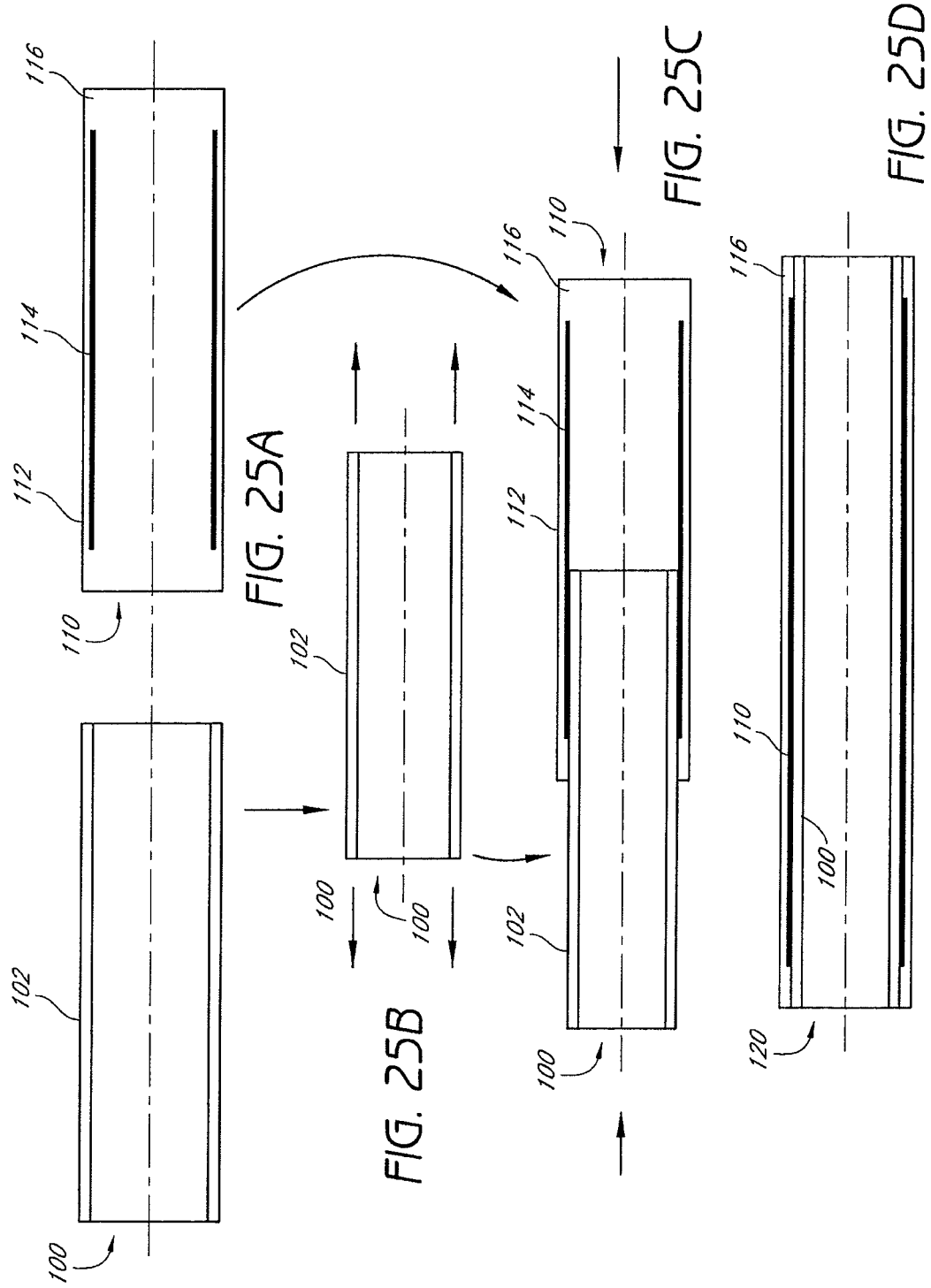

METHODS FOR MANUFACTURING MULTI-LAYER BALLOONS FOR MEDICAL APPLICATIONS

CROSS-REFERENCE TO RELATED APPLICATIONS

This application is a continuation of U.S. patent application Ser. No. 14/065,243 filed Oct. 28, 2013 and currently pending, which is a continuation of U.S. patent application Ser. No. 13/108,868 filed May 16, 2011, which issued on Oct. 29, 2013 as U.S. Pat. No. 8,568,648, which is a divisional of U.S. patent application Ser. No. 11/611,748, filed Dec. 15, 2006, which issued on May 17, 2011 as U.S. Pat. No. 7,942,847 and which claims priority under 35 U.S.C. § 119(e) to U.S. Provisional Application Ser. No. 60/751,014 filed on Dec. 16, 2005, entitled "Very High Pressure Multi-Layer Balloons for Medical Applications and Methods for Manufacturing Same," and to U.S. Provisional Application Ser. No. 60/831,529 filed on Jul. 18, 2006, entitled "Multi-Layer Balloons for Medical Applications and Methods for Manufacturing the Same," all of which are incorporated herein by reference in their entireties.

BACKGROUND

Field

Embodiments of this invention relate generally to balloon catheters and methods for making balloon catheters for medical applications. In particular, embodiments of this invention relate to multi-layer balloon catheters having at least two structural layers and at least one lubricating layer that can be formed through a nesting method.

Description of the Related Art

An increasing number of surgical procedures involve percutaneously inserted devices that employ an inflatable thin wall polymer balloon attached to the distal end of a small diameter hollow shaft called a catheter. The device can be advanced to the treatment site via an artery, vein, urethra, or other available passage beneath the skin. The shaft usually exceeds 130 cm in length so that the balloon can be positioned deep within the patient's body. The opposite (proximal) end of the shaft, typically having an inflation connector, remains external to the patient.

When a balloon is advanced to a treatment site, the balloon is deflated and tightly wrapped around the shaft to minimize its cross-section and facilitate easy insertion and navigation through the passage. After reaching the desired location, the balloon is slowly inflated with a high pressure saline solution. The balloon walls unfold and expand radially. During this process a substantial radial force can be exerted by or on the balloon walls. This hydraulically generated radial force can be utilized for a number of different medical procedures such as, for example, vessel dilation, stent deployment, passage occlusion, and bone compression or distraction (such as distraction of vertebrae in the spinal column).

Several factors can limit the force a balloon can exert while within a patient. For example, for a particular cross-sectional balloon size, the design of a balloon, the material used to construct the balloon, and the structural integrity of a balloon can limit the force a balloon can exert without failing (e.g., bursting). Minimizing the risk of balloon bursting can be important in many medical procedures because, upon bursting, balloon debris may become lodged within a patient causing potentially severe trauma. Additional, higher pressures may be needed to affect the treatment.

The hydraulically generated pressure, as noted above, typically exerts two types of stress on the balloon. Radial stress (or hoop stress) pushes a cylindrically-shaped balloon radially outward. Radial stress can lead to axial bursting of the balloon parallel to its longitudinal axis. Axial stress, on the other hand, pushes a cylindrically-shaped balloon axially outward. Axial stress can lead to radial bursting of the balloon somewhere along the balloon's circumference (e.g., complete fracture of the balloon).

Both radial stress and axial stress have a linear relationship in pressure to the balloon's wall thickness and the ratio of the balloon's diameter to the balloon's wall thickness. As a result, any increase in pressure or diameter size requires an equally proportional increase in the balloon's thickness to avoid a critical pressure level (i.e., burst pressure) that will cause the balloon to burst. Generally, radial stress is twice as large as axial stress, so balloons will frequently burst axially absent some deformity or preprocessing. However, in the presence of balloon deformities, a balloon may burst radially. Such a radial bursting could disadvantageously leave separated sections of the balloon inside the patient after the catheter is removed.

Increasing balloon wall thickness also increases the cross-section of the balloon when deflated and wrapped for insertion. Consequently, a balloon having an increased balloon wall thickness might have limited access to certain areas in a patient due to the balloon's increased size. Typically, the balloon's stiffness varies as a cube of the balloon's thickness. For example, doubling the balloon's wall thickness results in doubling the burst pressure or the balloon diameter without bursting, but also increases the stiffness by a factor of eight. This added wall stiffness impairs one's ability to tightly wrap the balloon around the catheter shaft, which is necessary to limit the size of the balloon's cross-sectional area. If the balloon is bent too much beyond its stiffness, undesirable deformities may result. Usually, a balloon having a wall thickness of less than 0.0022 inches must be used to avoid the above-mentioned problems.

Balloon deformities can be caused in many situations such as during formation, by scratching, by stretching, or by bending. These deformities lead to a concentration of stress when the balloon is subject to pressure, which can lead to further deformation and ultimately a lower critical burst pressure. Scratching of the balloon by a device attached to the catheter, such as a stent, is a relatively common concern.

A number of techniques are being used to modify balloon properties in order to improve balloon functionality. These techniques include blending different types of polymers, adding plasticizers to balloons, and modifying parameters of the balloon forming process. These methods are often not entirely successful in creating a more desirable balloon with improved mechanical characteristics. Typically, these known techniques improve one balloon performance parameter while deteriorating another parameter.

Some have attempted to resolve this problem by using multi-layer balloons. For the reasons described below, these prior art multi-layer balloons also have serious deficiencies.

SUMMARY

One aspect of embodiments of the present invention involves creating multi-layer balloons where each layer is made from tubing that optimizes the inner wall stretch thus providing maximum balloon strength. The multi-layer balloons have very high pressure ratings and toughness, yet excellent folding characteristics. Methods for producing such multi-layer balloons using existing balloon forming equipment are also provided.

Another aspect comprises a balloon with two structural layers having a slip layer disposed between the structural layers. The slip layer advantageously allows sliding between adjacent layers. As a result, flexibility of the multi-layer balloon is increased over single layer balloons having an equal wall thickness. Other aspects involve a different number of structural layers and lubricating layers, such as, for example, three structural layers and two lubricating layers, four structural layers and three lubricating layers, and five structural layers and four lubricating layers.

Another aspect involves a multi-layer balloon where each balloon layer has the same size (e.g., diameter and/or wall thickness), is comprised of the same material or materials having substantially identical mechanical properties, and has the same degree of molecular orientation in the body portion of the balloon. It will be apparent that in some situations it will be desirable to have some balloon layers having different sizes, materials, and/or degree of molecular orientations upon deflation, while at the same time having equivalent size, mechanical properties, and/or orientation upon inflation. For other applications, it will be apparent that one can vary size, material, and/or orientation to at least some degree while still remaining within the spirit of the invention.

Another aspect comprises a balloon with a plurality of layers, wherein at least one structural layer has low friction surfaces. It will be apparent that further variations are possible involving different combinations of lubricating layers and structural layers. These lubricating and structural layers need not be in an alternating configuration.

In yet another aspect, structural layers can be polyamides, polyesters, polyethylenes, polyurethanes and their co-polymers. It will be apparent that further variations are possible involving structural layers of other material or chemical composition.

In one aspect of embodiments of the present invention, the layers can be adapted to the particular stresses, pressures, and deformities to which they might be vulnerable. For example, because the top layer might be exposed to sharp objects (such as stents, calcified plaque, bone, or other natural protrusions within a patient's body), the top layer could be made from a more compliant material that is scratch resistant. The inner layers of the multi-layer balloon, which are generally not exposed to sharp objects, could be made from a less compliant material with a higher burst strength. It will be apparent that further variations are possible, depending on which stresses, pressures, and deformities the layers must withstand in a particular medical application.

In another aspect, lubricating layers can be silicon oil, "bucky balls" (carbon nanopowder), high-density polyethylene, tetrafluoroethylene, or a mixture thereof. It will be apparent that further variations are possible involving lubricating layers of other material or chemical composition.

Another aspect involves a method for creating multi-layer balloons with low friction interfaces by nesting multiple balloons or by nesting co-extruded tubing. It will be apparent that these methods can be combined with each other and other balloon forming methods to produce larger multi-layer balloons.

In one aspect, the bodies of the balloons can be extruded separately on the same mold to ensure that they have equivalent, or substantially equivalent, size. The necks, however, might need to be different sizes to ensure optimal welding and/or attachment to the catheter. It will be apparent that other methods can be used to obtain approximately equivalent sized balloons. It will also be apparent that similar results can be achieved by making the outer balloon wider than the inner balloon.

In another aspect, separately formed balloons can be nested after altering the orientation of one balloon to make it thinner, facilitating insertion. One way to accomplish this is by axial stretching. It will be apparent that other methods can be used to make a balloon thinner.

In another aspect, already nested balloons can be heated, stretched, and inflated simultaneously to achieve optimal molecular alignment. It will be apparent that this need not be done simultaneously, especially when nesting can be done after the balloons are heated, stretched, and inflated to equivalent size and orientation. Similarly, it will be apparent that the balloons need not be formed and processed identically to obtain equivalent burst strengths, sizes, and/or molecular orientations. This is especially true for balloons of different materials. Other suitable methods can also be used to achieve uniform molecular alignment among the balloon layers.

In yet another aspect, lubricant can be added at any stage of the multi-layer balloon forming process. The lubricant can be co-extruded onto or between balloon layers, applied to balloon layers after extrusion but before nesting, or injected between balloon layers after nesting. In one embodiment, lubricant can be kept separate from certain regions of the balloon. This can be valuable to promote friction in that area if desired. This can also be valuable if the lubricant interferes with welding the balloon layers to each other or to the catheter. In another embodiment, lubricant can be distributed between the balloon layers before or after balloon welding. It will be apparent that this can be accomplished under a wide variety of methods.

In another aspect of embodiments of the present invention, already nested or co-extruded balloons can be treated as a single balloon in the context of this invention. As a result, one can manufacture balloons with a greater numbers of layers than those specifically disclosed herein.

In another aspect of embodiments of the present invention, tubing for the outer balloon can be co-extruded with a lubricious layer on its inside wall. Tubing for the inner balloon, which would not possess a lubricious layer, can be stretch longitudinally to fit within the tube for the outer balloon. This nested tube arrangement can then be used to blow a balloon in a single process. Note that longitudinal stretch does not affect the tubing's radial stretch. This embodiment is an important consideration because trying to longitudinally stretch a tube with a co-extruded lubricious layer, such as by stretching a tube with a lubricious outer layer to nest within another tube, would result in sagging or separation of the lubricious layer.

BRIEF DESCRIPTION OF THE DRAWINGS

These and other features, aspects, and advantages of the present invention will now be described in connection with preferred embodiments of the invention shown in the accompanying drawings. The illustrated embodiments, however, are merely an example and are not intended to limit the invention. The drawings include twenty-five figures, which are briefly described as follows:

FIG. 4 is an enlarged cross-sectional view of a fluted balloon catheter that has developed a crack deformity upon wrapping.

FIG. 5 is a perspective view of a balloon catheter that has developed a scratch deformity.

FIG. 6 is a perspective view of a balloon catheter that has developed a cat-eye deformity.

FIG. 10 shows that once optimal stretch is achieved, a balloon material will have its greatest strength and will resist further growth.

FIG. 17 shows the inner stretch of wall slices of the two-layer balloon relative to the inner stretch of corresponding wall slices of the single-layer balloon.

FIG. 18 shows the inner stretch of wall slices of each layer of the two-layer balloon relative to the inner stretch of corresponding wall slices of the single-layer balloon.

FIG. 19A is a perspective view of a balloon catheter having an element shown aligned in a longitudinal direction and in a lateral direction.

FIG. 19B is an enlarged perspective view of the longitudinally-aligned element of the balloon catheter as shown in FIG. 19A.

FIG. 23A is a side elevational view of a three layer balloon and a two layer balloon used in a method for co-extruding balloons to form a multi-layer balloon.

FIG. 23B is a side elevational view of the three layer balloon after heating and stretching so as to the decrease the diameter of the three layer balloon prior to insertion into the two layer balloon of the method for co-extruding multi-layer balloons of FIG. 23A.

FIG. 23C is a side elevational view of the three layer balloon having a decreased diameter being inserted into the two layer balloon having its original diameter of the method for co-extruding multi-layer balloons of FIG. 23A.

FIG. 23D is a side elevational view of a multi-layer balloon having five layers after heating, stretching, and inflating so that the three layer balloon component and the two layer balloon component have the same, or a substantially similar, degree of molecular alignment of the method for co-extruding multi-layer balloons of FIG. 23A.

FIG. 24A is a side elevational view of a multi-layer balloon formed using the methods disclosed showing a method for welding the necks of the multi-layer balloon in order to securely attach the balloon layers to each other.

FIG. 24B is a side elevational view of the multi-layer balloon having its necks welded of FIG. 24A.

FIG. 25A is a side elevational view of a single-layer tubular extrusion without a slip layer and a single-layer tubular extrusion of the same size having a slip layer on its inner surface used in a method to form a two-layer high pressure balloon.

FIG. 25B is a side elevational view of the single-layer tubing without a slip layer after axial stretching to decrease its diameter prior to insertion into the single-layer extrusion having a slip layer on its inner surface in the method for nesting two-layer balloons of FIG. 25A.

FIG. 25C is a side elevational view of the single-layer extrusion having a decreased diameter being inserted into the single-layer extrusion having its original diameter in the method for nesting two-layer balloons of FIG. 25A.

FIG. 25D is a side elevational view of a two-layer parison comprising a first balloon layer, a slip layer, and a second balloon layer such that the first balloon layer and the second balloon layer have the same, or a substantially similar, degree of molecular alignment in the method for nesting two-layer balloons of FIG. 25A.

DETAILED DESCRIPTION

Embodiments of the present invention will now be described more fully hereinafter with reference to accompanying drawings, in which preferred embodiments are shown. This invention may, however, be embodied in many different forms and should not be construed as limited to the embodiments set forth herein; rather, these embodiments are provided so that this disclosure will be thorough and exemplary of the scope of the invention to those skilled in the art.

Figure 1:
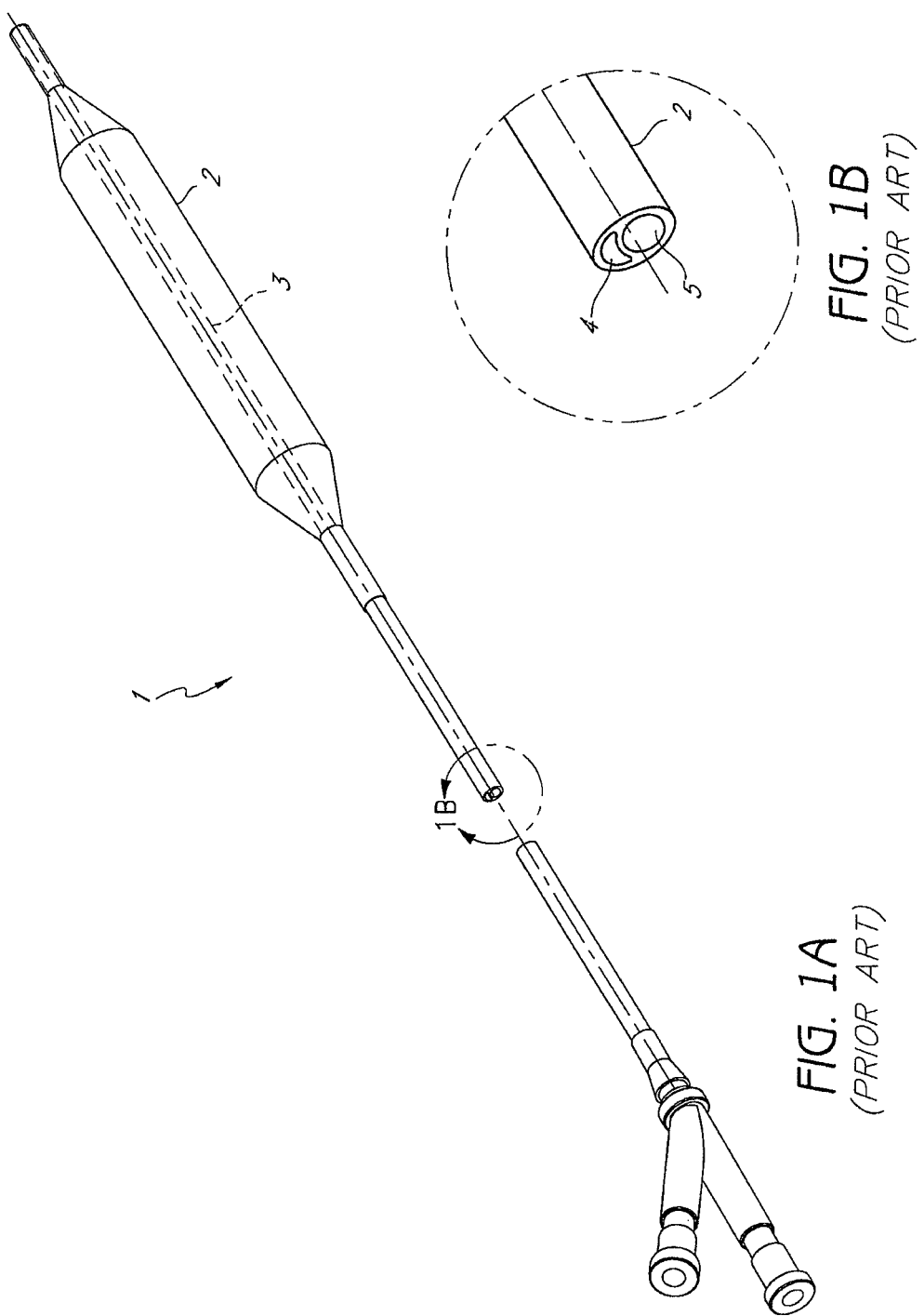
FIG. 1A is a perspective view of an exemplary prior art balloon catheter.
FIG. 1B is an enlarged perspective view of a cross-section of a prior art balloon catheter shaft.

FIGS. 1A and 1B show an exemplary embodiment of a prior art balloon catheter system 1. A balloon 2 is attached to the distal end of a catheter shaft 3 and is inflated through an inflation lumen 4. A guide wire lumen 5 is provided on the catheter system 1, which allows for external control of the balloon 2 and the catheter 3 when the system 1 is disposed within a patient. It should be noted that further variations (e.g., rapid exchange, concentric lumen, etc.) are possible for this structure.

Figure 2:
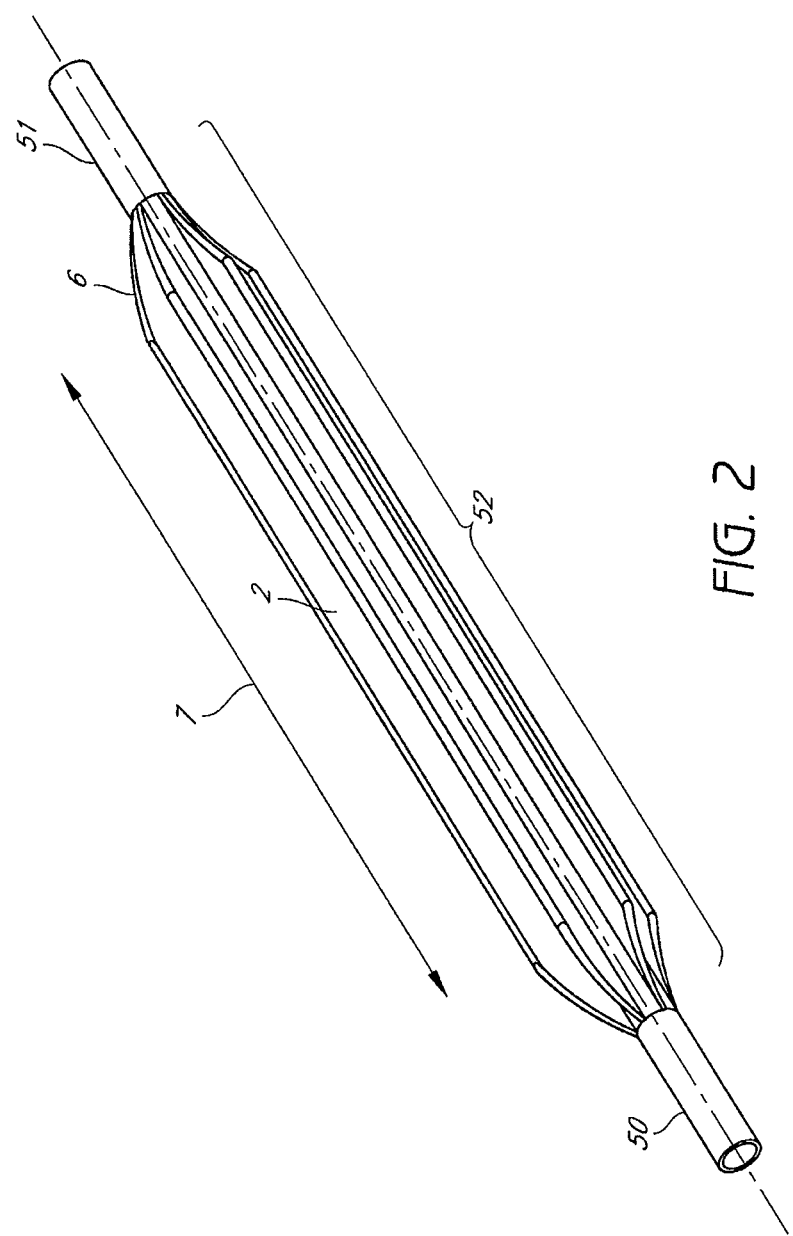
FIG. 2 is a perspective view of a balloon catheter having a plurality of flutes.

FIG. 2 illustrates a perspective view of an embodiment of a prior art catheter balloon 2 in an unwrapped and deflated configuration. The balloon 2 is folded into a plurality of flutes 6, typically ranging from three to eight flutes. The plurality of flutes 6 are formed in a direction substantially parallel to a longitudinal direction of the balloon 7. The plurality of flutes 6 are folded with a slight curvature in order to facilitate subsequently wrapping the fluted balloon 2 around the catheter shaft 3 (as shown in FIG. 1A). The balloon 2 attaches to the catheter shaft 3 both at a proximal neck of the balloon 50 and at a distal neck of the balloon 51. The balloon 2 also includes a body portion 52, which can be inflated and deflated when the balloon 2 is disposed within the body of a patient during a particular medical procedure.

Figure 3B:
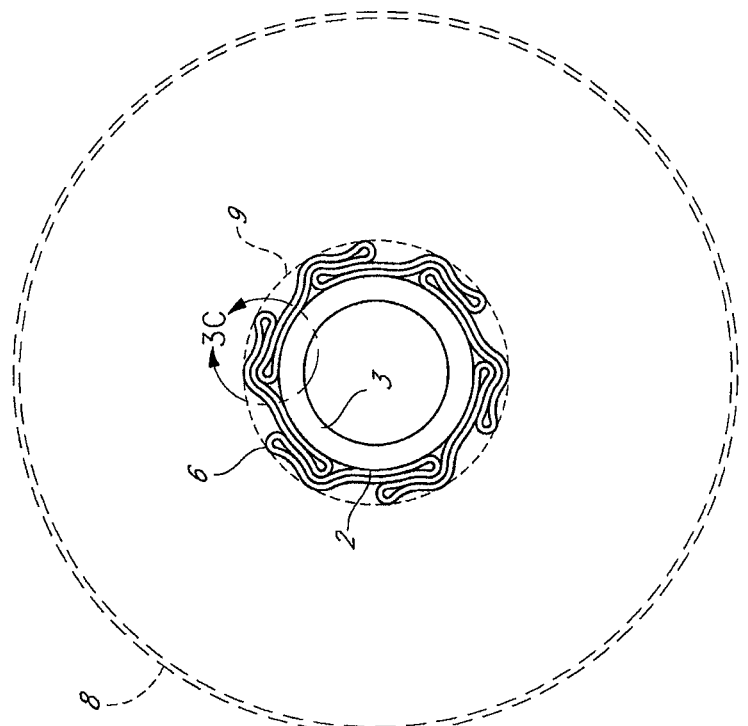
FIG. 3B is a cross-sectional view of a fluted balloon catheter after wrapping.
Figure 3A:
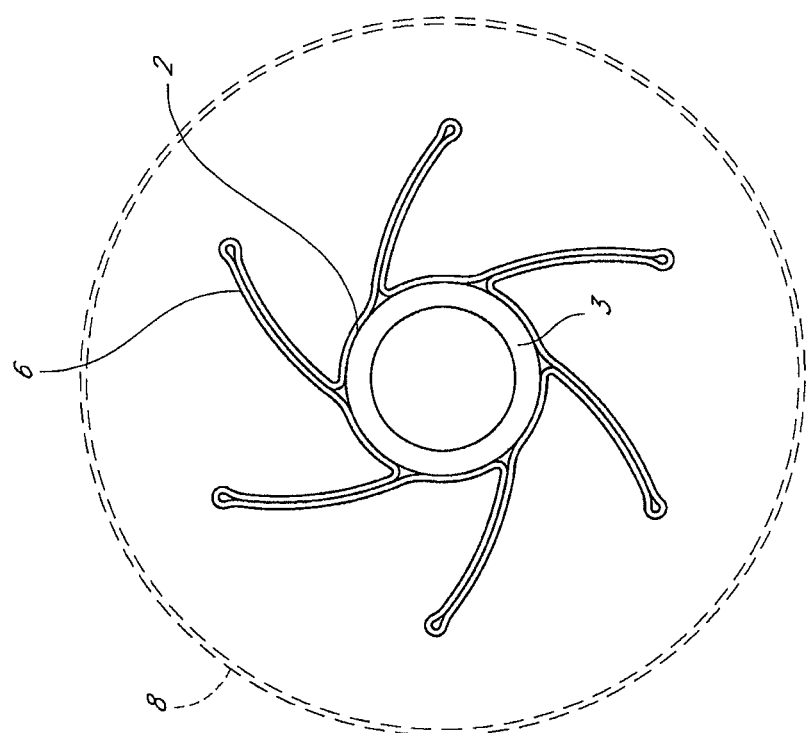
FIG. 3A is a cross-sectional view of a fluted balloon catheter before wrapping has been performed.

FIG. 3A shows a cross-section of an embodiment of a prior art fluted balloon 2 on a catheter shaft 3. The fluted balloon 2 has a plurality of flutes 6. In the illustrated embodiment, the plurality of flutes 6 comprises six flutes. The deflated fluted balloon 2 has a relatively small cross-sectional area, but can have a relatively wide diameter because the thin flutes 6 stretch radially outward from the catheter shaft 3. Upon inflation, the balloon 2 can expand to have a much larger diameter and cross-sectional area 8, as shown in the circular phantom lines in FIG. 3A.

FIG. 3B shows a cross-section of an embodiment of a prior art fluted balloon 2 after it has been wrapped. The plurality of flutes 6 are folded down and about the catheter shaft 3 such that they are in close contact with each other and the catheter shaft 3. Once the balloon 2 is wrapped, the deflated balloon's diameter and cross-sectional area 9 (sometimes referred to as the crossing profile) is much smaller than the inflated balloon's diameter and cross-sectional area 8 (as seen in the circular phantom lines in FIG. 3B). Having a balloon 2 with a small diameter and cross-sectional area 9 allows the catheter 2 to be guided through smaller passageways within a patient's body. Inflating the balloon 2 to have a larger diameter and cross-sectional area 8 advantageously allows for the placement of a larger stent, occlusion of a larger passageway, and generally greater versatility once the catheter 2 has reached a particular treatment site within a patient's body.

Figure 3C:
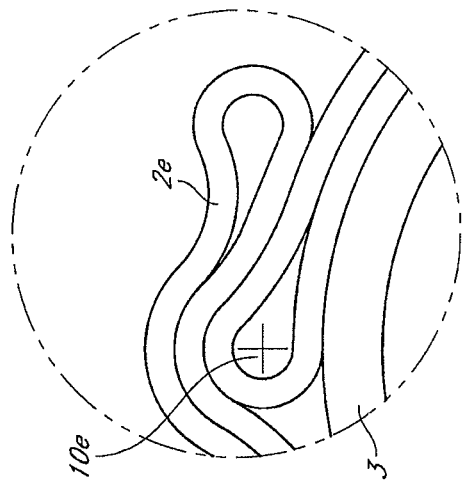
FIGS. 3C through 3E are enlarged cross-sectional views of three different fluted balloon catheters after wrapping.
Figure 3D:
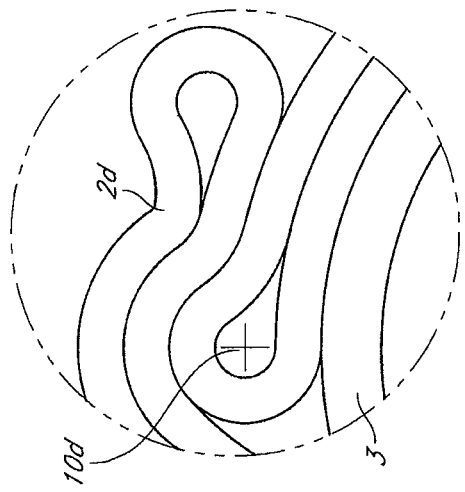
Figure 3E:
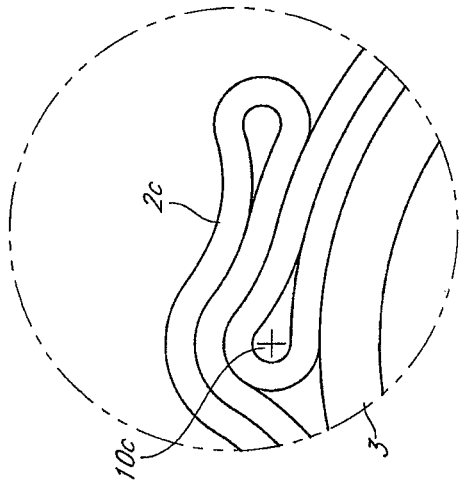

FIGS. 3C through 3E generally illustrate enlarged views of several configurations of balloon folding patterns. FIG. 3C illustrates an enlarged side elevational view of a cross-section of a prior art fluted balloon 2c after wrapping. As shown in FIG. 3C, the reduction in size of the wrapped balloon 2c about the catheter shaft 3 is limited by the balloon's bend radius 10c. In general, a balloon's bend radius increases with the thickness and toughness of the balloon, as can be seen by comparing FIG. 3C with FIGS. 3D and 3E. FIG. 3D shows a balloon 2d that is thicker than the balloon 2c shown in FIG. 3C. As can be seen in FIG. 3D, the bend radius 10d for the thicker balloon 2d is larger than the bend radius of the balloon 2c in FIG. 3C. FIG. 3E shows a balloon 2e having the same thickness as the balloon 2c of FIG. 3C, but being composed of a tougher material than that of the balloon in FIG. 3C. As can be seen in FIG. 3E, the bend radius 10e for the tougher balloon 2e is also larger than the bend radius of the balloon 2c in FIG. 3C. Accordingly, both a thicker balloon 2d and a tougher balloon 2e typically cannot be folded into as small a cross-section as the balloon 2c of FIG. 3C. The bend radius of a balloon is important because bending a balloon beyond its bend radius can cause deformities which will lower the balloon's resistance to bursting when inflated.

Figure 3F:
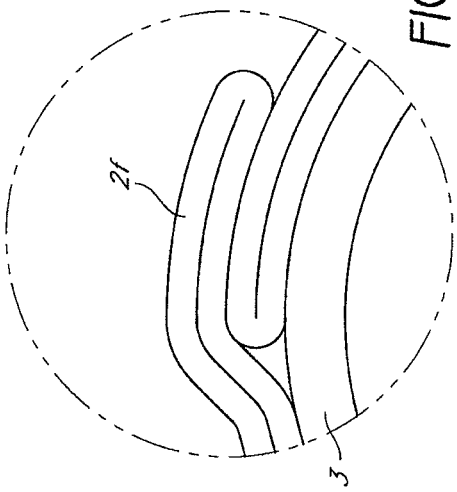
FIG. 3F is an enlarged cross-sectional view of a fluted balloon catheter after wrapping and compression.

FIG. 3F shows a balloon 2f wrapped about a catheter shaft 3. The balloon 2f has a negligible bend radius and can, therefore, be tightly wrapped about the catheter shaft 3 without any protrusions developing on the outer surface of the folded and wrapped balloon 2f. Advantageously, this configuration permits the diameter and the cross-section of the balloon 2f to be minimized prior to, and during, insertion of the balloon catheter system into a patient's body. In addition, as discussed in further detail below, this configuration minimizes failure of the balloon 2f during a medical application due to a deformity developing on the balloon's outer surface.

FIGS. 4 through 6 generally show deformities that can develop on a balloon's outer surface. As shown in FIG. 4, a wrapped balloon 2 is folded and compressed beyond its bend radius 10 creating a crack 11 in the outer surface of the wrapped balloon 2 near the site of a fold. Such cracking is more likely for less compliant materials, which also generally have higher burst strengths. Thus, there is a general trade off between burst strength and flexibility. Once the crack 11 has formed, stress will concentrate near the crack 11 when the balloon 2 is inflated, causing the crack 11 to expand and ultimately causing failure of the balloon 2 (e.g., by bursting).

FIG. 5 shows another deformity that occurs in balloons. When a medical device such as a stent is applied over a balloon 2, it can create a scratch 12. The scratch 12 generally extends in the longitudinal direction of the balloon 2. Again, the likelihood of scratching can be minimized by using a more compliant material, which also has a lower burst strength. Once the scratch 12 has formed, stress will concentrate near the scratch 12 when the balloon 2 is inflated, causing the scratch 12 to expand and ultimately causing failure of the balloon 2 (e.g., by bursting).

FIG. 6 illustrates yet another type of deformity. When a balloon is formed, there may be regions of low molecular density or imperfections in the molecular lattice. As a result, a small hole 13 can form upon stretching the balloon 2. The hole 13 can grow as the balloon 2 is stretched further, often resembling a "cat-eye." Stress concentrates near the edges of the cat-eye deformity 13. Since the balloon 2 is stretched during inflation, this can also lead to failure of the balloon 2 (e.g., by bursting).

Figure 7A:
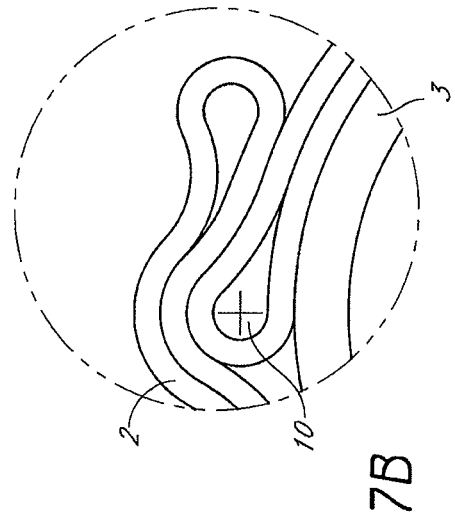
FIG. 7A is an enlarged cross-sectional view of a fluted multi-layer balloon catheter after wrapping.
Figure 8A:
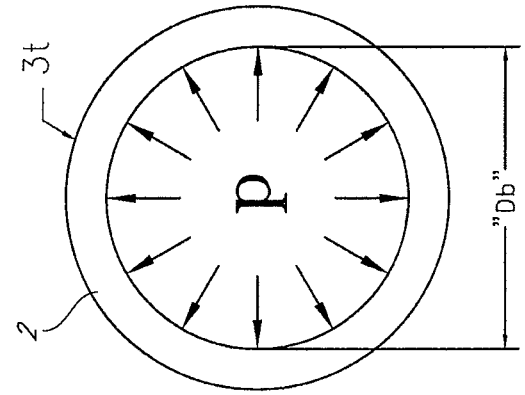
FIG. 8A is a cross-sectional view of a multi-layer balloon catheter after inflation.

FIGS. 7A and 8A show an enlarged cross-section of an embodiment of a multi-layer balloon 2 having a first layer 20, a second layer 22, and a third layer 24. In one embodiment, in which the multi-layer balloon 2 comprises a balloon having three structural layers, the first layer 20 comprises a top layer of the multi-layer balloon, the second layer 22 comprises a middle layer of the multi-layer balloon, and the third layer 24 comprises a bottom layer of the multi-layer balloon. The multi-layer balloon 2 is shown in the wrapped position, similar to position illustrated in FIG. 3C. The first layer 20 of the multi-layer balloon has a thickness that is approximately one-third the thickness of the single-layer balloon shown in FIG. 3C. The second layer 22 and the third layer 24 also each have a thickness that is approximately one-third the thickness of the single-layer balloon shown in FIG. 3C. Because each layer 20, 22, 24 is thinner than the single-layer balloon of FIG. 3C, the bend radius 10 is smaller for an equal cumulative thickness 3*t*. Because the cumulative thickness of the multi-layer balloon 2 of FIG. 7A is substantially the same as the thickness of the single-layer balloon of FIG. 3C, the burst pressure P will also be the substantially the same as long as adjacent balloon layers of the multi-layer balloon can slide relative to each other.

Figure 7B:
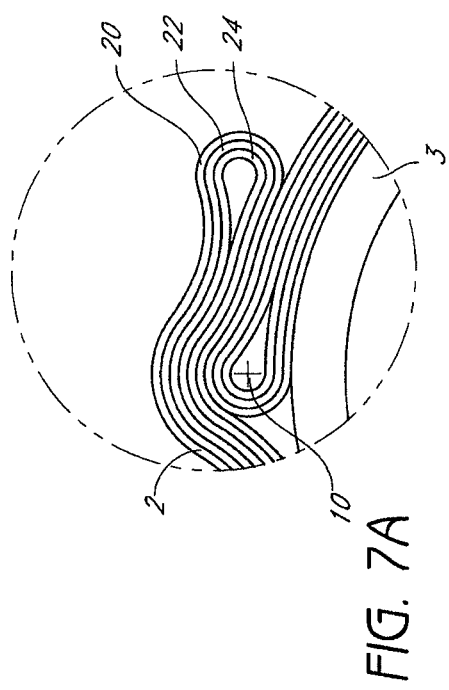
FIG. 7B is an enlarged cross-sectional view of a fluted single layer balloon catheter after wrapping.
Figure 8B:
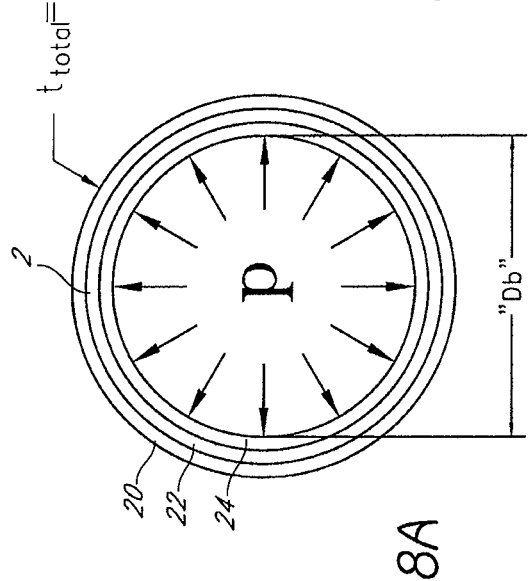
FIG. 8B is a cross-sectional view of a single layer balloon catheter after inflation.

As shown in FIGS. 7B and 8B, a balloon 2 with a single layer has a total thickness 3*t* that is equivalent to the thickness of the multi-layer balloon 2 shown in FIGS. 7A and 8A. As shown in FIG. 7B, the thicker balloon 2 has a larger bend radius 10, and thus cannot be folded as closely to the catheter shaft 3. If a scratch develops on the first layer 20 of the multi-layer balloon during the crimping and wrapping process, the first layer 20 could burst while, at the same time, the other balloon layers 22, 24 retain their structural integrity. More generally, a single balloon layer 20, 22, 24 might fail as a result of a deformity, such as those shown in FIGS. 4 through 6, on any layer 20, 22, 24. As a result, the multi-layer design provides redundancy that could be valuable in certain medical procedures. Furthermore, because the multi-layer design is more flexible, as discussed below, deformities as shown in FIG. 4 are less likely to occur. Meanwhile, the burst pressure P for a multi-layer balloon is substantially the same as that for an equivalent thickness single layer balloon, as can be seen by comparing FIG. 8A with FIG. 8B. It will be apparent that similar effects can be achieved by varying the material in each balloon layer, varying the number of balloon layers, and varying other aspects of this embodiment.

In one embodiment, the first layer 20 of the multi-layer balloon is made of a soft material that is preferably scratch and puncture resistant. When a device such as a stent is applied to the catheter system, it is typically crimped onto the balloon 2. The applied crimping force should be such as to provide a sufficiently strong attachment force, yet it should also not scratch, pierce, or otherwise damage the balloon wall. By using a softer first layer 20 (which can comprise an outer layer of the multi-layer balloon), the risk of failure due to scratching can be decreased.

The second layer 22 and the third layer 24 (which can comprise inner layers of the multi-layer balloon) can be made of a tougher material that is less scratch resistant, but able to withstand higher applied pressures. These layers 22, 24 can be protected from scratching by the soft outer layer 20, but still can provide additional strength to the multi-layer balloon. It should be noted that the above-described effects need not always be achieved simultaneously, and they are not necessarily sensitive to the number of layers, composition of other layers, form of device carried by the catheter, or other aspects of this embodiment.

As is discussed in greater detail below, each layer 20, 22, 24 may be equally sized and shaped in the body portion 52, in order to optimize the burst characteristics of the balloon in accordance with the present invention. As the balloon is inflated, each layer is stretched, causing the thickness to shrink. This causes the third balloon layer 24 to stretch approximately as far as the first balloon layer 20. If the third balloon layer 24 begins with a smaller diameter than that of the first layer 20, then the third layer 24 must stretch an additional amount to match the size of the first balloon layer 20. This can cause the inner balloon layers 22, 24 to burst before the outer balloon layer 20, which can limit the multi-layer balloon's maximum inflation to a level that inflates the larger outer balloon layer 20 below its optimal inflation level. Consequently, using substantially identical balloons for each layer of the multi-layer balloon makes each balloon layer have a substantially similar burst pressure, ensuring that they burst substantially simultaneously and reducing the possibility of sub-optimal inflation of any layer 20, 22, 24 of the multi-layer balloon. It will be apparent that balloons of different material may require different sizes and shapes to achieve this effect. It will also be apparent that, because the balloons still do not stretch to exactly equal diameters upon inflation, it may be practical to make the inner balloons slightly smaller such that each layer stretches to substantially near its optimal inflation level.

One general problem with multi-layer balloons is that the interior balloon layer often bursts before the exterior balloon layer. This occurs because the outer layers have not been optimized for maximum wall strength.

The interior balloon layer bursts prior to exterior balloon layers because the multi-layer balloon does not comprise layers having uniform burst strengths. This is primarily a result of not taking into account the confounding effect of radial expansion on achieving optimal radial stretch during the balloon blow molding process.

Figure 9:
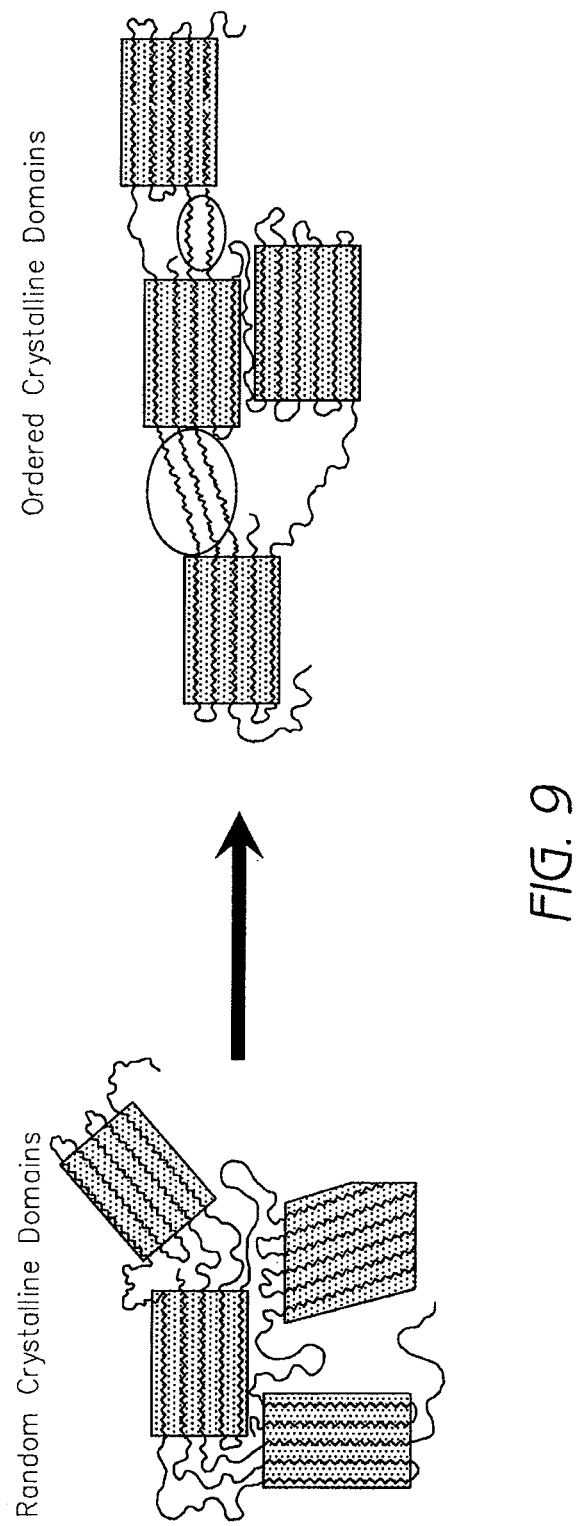
FIG. 9 is a schematic showing the stretching of polymers to align their molecular chains through a blow molding process.
Figure 10:
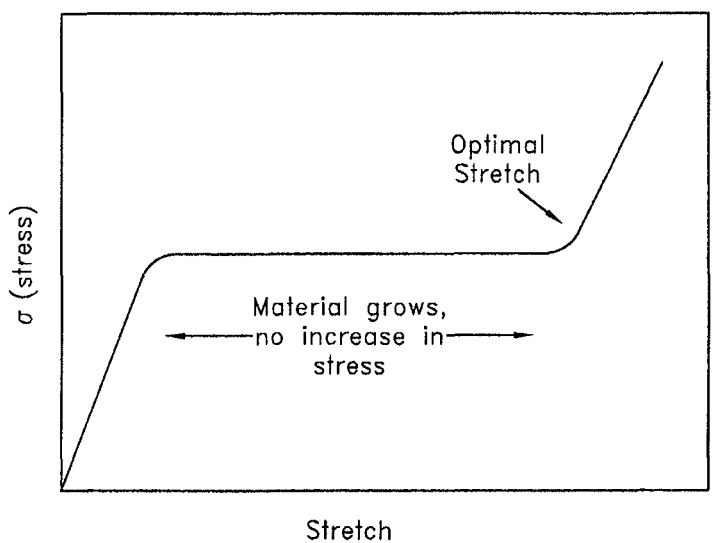
FIG. 10 is a stress-strain curve with strain, or the amount that a balloon will stretch, on the x-axis and stress, or the applied pressure, on the y-axis.

With reference to FIGS. 9 and 10, an objective of blow molding in balloon formation is to stretch the polymer material in order to achieve maximum strength and semi-compliance. This is done by aligning the molecular chains as shown in FIG. 9. During the stretching process, the material will grow until the polymer chains are aligned. Once the polymer chains are aligned, the material resists further growth and provides maximum strength. This is shown on the idealized stress-strain curve in FIG. 10. In response to the strain caused by stretching, the material exhibits relatively even stress. Once the polymer chains are aligned, the material resists further growth as shown by an increase in stress. In the ideal cases, all polymer chains will be uniformly stretched. Various polymer materials will have different ideal stretch ratios in order to achieve uniform molecular alignment.

Optimum stretch for a multi-layer, high-pressure, balloon is dependent upon a number of variables. For a given material, there is a calculated optimum stretch that provides optimum strength of the multi-layer balloon. The calculated optimum stretch is dependent upon, for example, the diameter of the balloon and the thickness of the layers which comprise the multi-layer, high-pressure, balloon. Practically, it is very difficult to stretch a balloon to its exact optimum stretch. Thus, for most applications, stretching a material to within 15% of its optimum stretch, and preferably to within less than 10%, will provide optimum balloon strength.

During the balloon forming process, the polymer material is stretched both radially and longitudinally in order to achieve biaxial orientation of the polymer chains. However, radial stress is twice that of longitudinal stress. As a result, optimizing the radial stretch is more important to burst resistance than longitudinal stretch.

Figure 11:
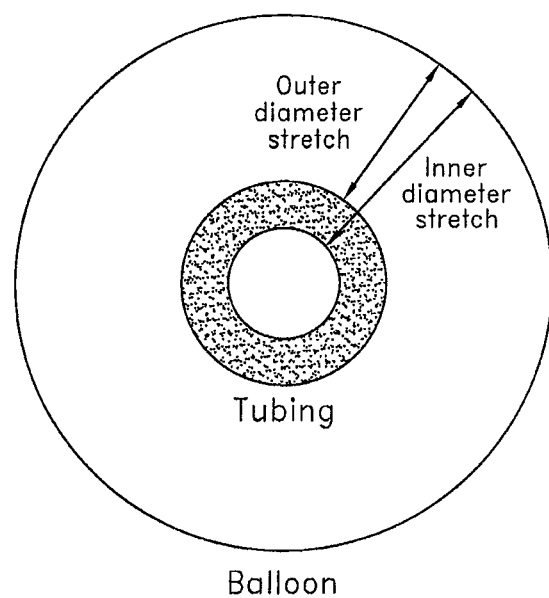
FIG. 11 is a diagram illustrating the inner diameter stretch and the outer diameter stretch of single-layer balloon tubing when expanded and showing that the outer diameter stretch is less than the inner diameter stretch.
Figure 12:
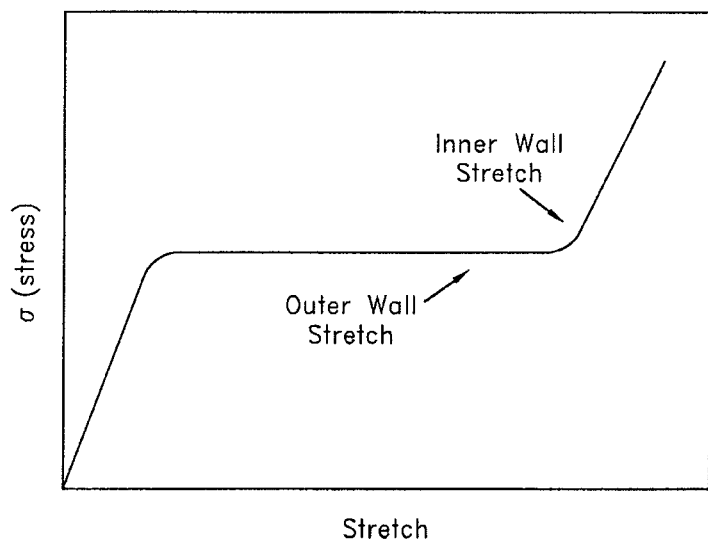
FIG. 12 is a stress-strain curve showing that when the inner wall stretch of single-layer balloon tubing is optimized, the outer wall stretch is sub-optimal and will continue to expand when applied pressure is increased.

With reference to FIGS. 11 and 12, radial stretch confounds the goal to achieve a uniform stretch of the polymer material. The reason for this is that balloons are blow molded from tubing having thicker walls. As shown in FIG. 11, because of the difference in wall thickness the stretch of the inner wall of the initial tubing to that of the balloon will be greater than that of the respective outer wall stretch. In view of the non-uniform stretch between the inner wall and the outer wall of the tubing, a problem encountered in the art is optimizing the radial stretch of the balloon tubing. If the outer wall stretch be optimized, then the inner wall becomes over-stretched. Consequently, the inner wall will develop micro-tears which can lead to premature failure of the balloon tubing. Therefore, a feasible solution to this problem is to optimize the radial stretch based on the inner wall rather than the outer wall.

As shown in the stress-strain curve in FIG. 12, the outer wall is under-stretched when optimizing radial stretch based upon the inner wall of the balloon. When the inner wall achieves optimal alignment of its polymer chains, as shown on the stress-strain curve, the outer wall has not yet reached optimal alignment of its polymer chains, as shown by being further down the stress-strain curve of FIG. 12. If the inner portion of the balloon wall fails, the outer portion will continue to stretch thus providing no additional strength to the balloon wall.

Figure 13:
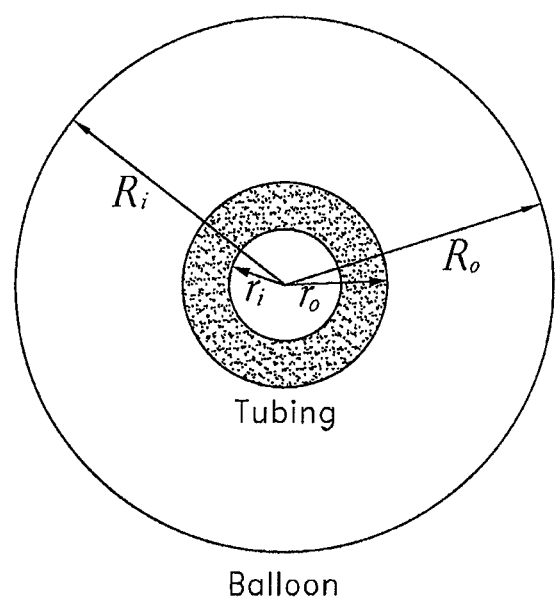
FIG. 13 is a diagram illustrating the inner and outer radii of single-layer balloon tubing in an unexpanded and an expanded state.

The relative under-stretching of the outer wall can be substantial. This can be shown using a mathematical model relating the radial expansion of a smaller-diameter hollow cylinder with a given wall thickness (the initial extruded tube) to a hollow cylinder with a larger diameter and thinner walls (the blow molded balloon body). FIG. 13 shows the various radii to be taken into account from a cross section of the tube and balloon. Of particular interest will be the inner wall stretch ($S_i = R_i/r_i$) and the outer wall stretch ($S_o = R_o/r_o$). As $S_i$ is given as being the optimized radial stretch, the relative ratio of $S_o/S_i$ will used to demonstrate the confounding effect of radial stretch on uniform wall strength.

Formula I, set forth below, shows the equation for the mass (M) of a hollow cylinder based on its radius (r), length (L) and density ($\rho$). In expanding the hollow cylinder represented by the tube to a balloon, the mass remains the same. Accordingly, there is a fixed relationship between the radii of tube to that of the balloon as shown in Formula II (the parameters with the subscripted t refers to the tubing and the subscripted B refers to the balloon). Thus, for a balloon of a given diameter ($R_o/2$) and wall thickness ($W_b$) with an optimized inner wall stretch, there is a specific tube size that must be used as a starting condition.

$$M = \pi(r_o^2 - r_i^2)L\rho \qquad \text{I.}$$

$$\pi(r_o^2 - r_i^2)L_t\rho_t = \pi(R_o^2 - R_i^2)L_B\rho_B \qquad \text{II.}$$

For a given balloon, the required inner radius for the tubing is simply the balloon outer radius less the wall thickness divided by the optimal stretch for the polymer used: $r_i = (R_o - W_b)/S_i$. Determining the outer tubing radius, $r_o$, is more complicated but can be derived from the equation in Formula II.

As set forth below, Formula III shows such a derivation with $S_L$ being used to express the longitudinal stretch ($S_L = L_B/L_t$) and $\rho$ the relative change in density ($\rho = \rho_B/\rho_t$). With these two equations, $S_o$ and $S_i$ can be calculated and the confounding effect of radial stretch shown.

$$r_o = \sqrt{S_L\rho(2R_oW_B - W_B^2) + (R_o - W_B)^2/S_i^2} \qquad \text{III.}$$

Figure 14:
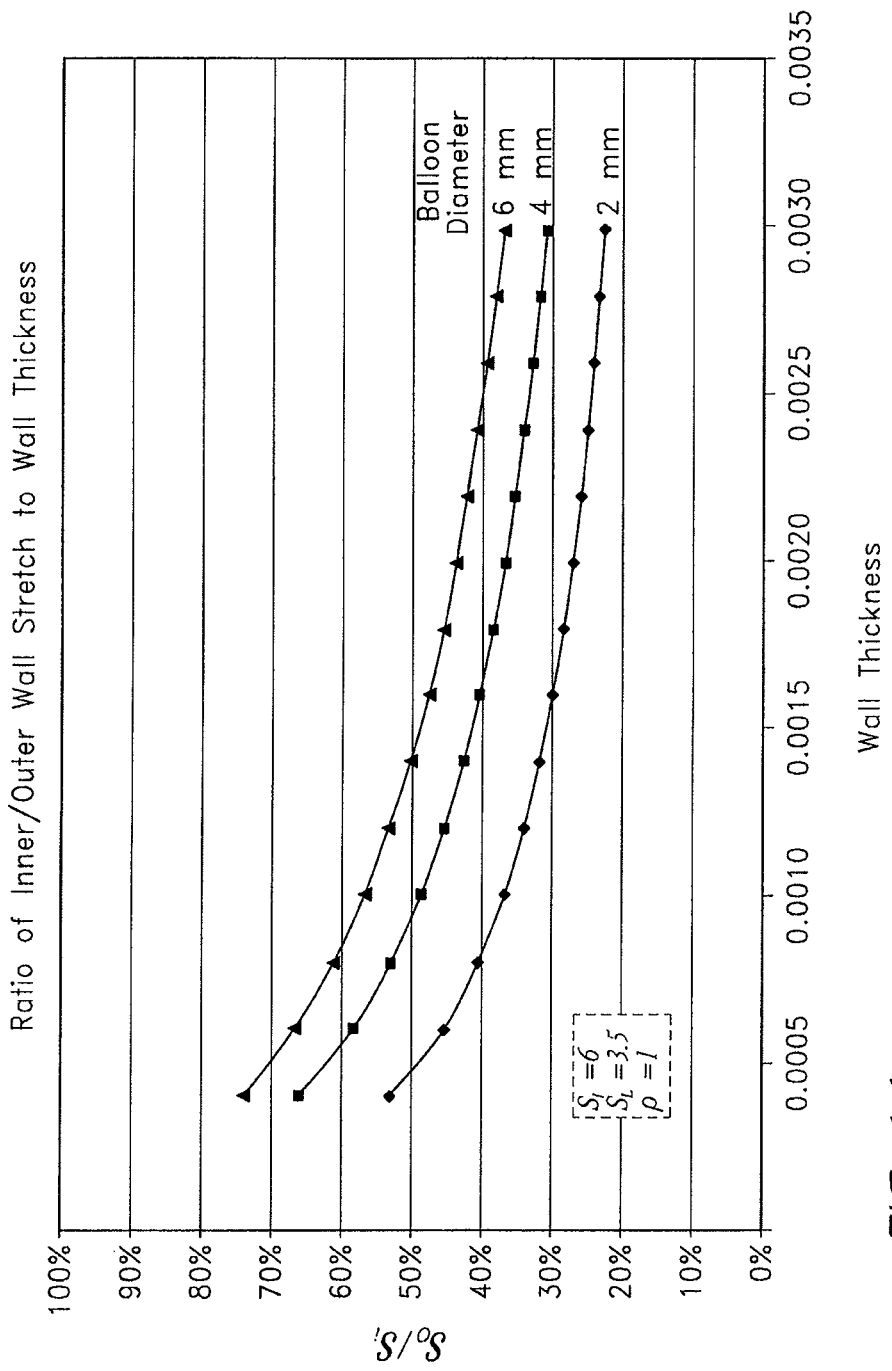
FIG. 14 is a graph showing single-layer balloon catheters having diameters of 2 mm, 4 mm, and 6 mm, with wall thickness on the x-axis and the ratio of inner wall stretch to outer wall stretch on the y-axis.

FIG. 14 shows the ratio of $S_o/S_i$ as a function of wall thickness for a number of different balloon diameters. As can be seen, the relative under-stretching of the outer wall can be substantial. For example, the outer wall for a 2 mm balloon with a wall thickness of 0.001 inches has been stretched less than 40% relative to the inner wall. Any increase in wall thickness to try to strengthen the wall shows a further decrease in relative stretching. The same 2 mm balloon with a 0.002 inch wall thickness shows a relative wall stretch of less than 30%.

Figures 15, 16:
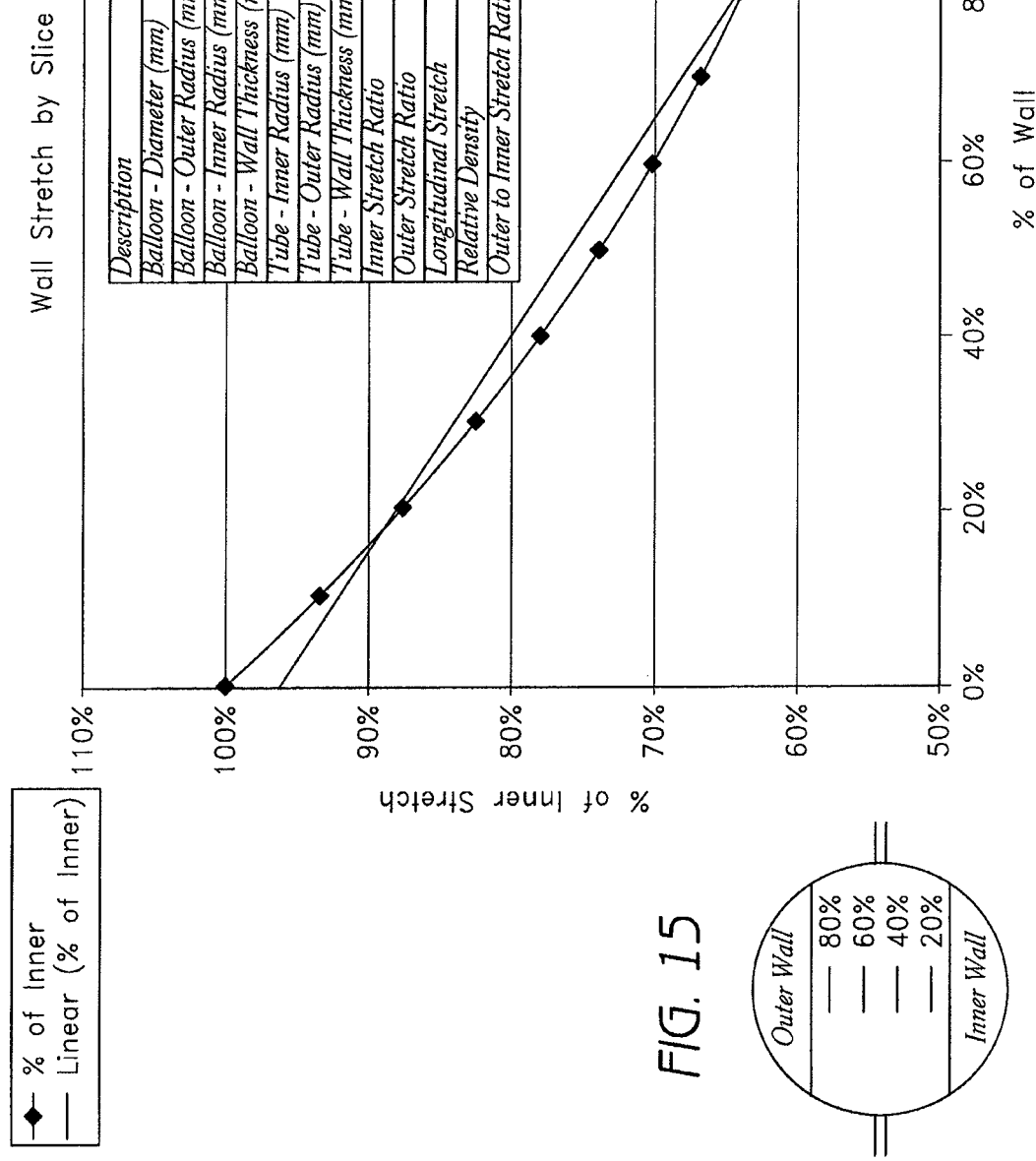
FIG. 15 is a schematic showing the wall profile of a single-layer balloon catheter that is represented in the graph of FIG. 16.
FIG. 16 is a graph of a single-layer balloon catheter showing the relative stretch ratio as a function of wall slice with wall position on the x-axis and percentage of inner balloon stretch on the y-axis.

Turning now to FIGS. 15 and 16, the confounding effect of radial stretch can be shown in more detail by examining the distribution of relative stretch within the wall. This can be done by "mapping" the respective wall slice in the tube to that of the balloon. FIG. 15 shows such a map in which the inner wall has a position of 0% and the outer wall has a position of 100%. By calculating the stretch of a slice for the tube wall, for example the 20% line, to the equivalent slice in the balloon, the distribution of relative radial stretch can be shown. FIG. 16 shows a graph of a representative balloon with the relative stretch ratio as a function of wall slice. As can be seen, the fall off in relative stretch is not proportional and in fact falls off more quickly from the inner wall.

Figure 17:
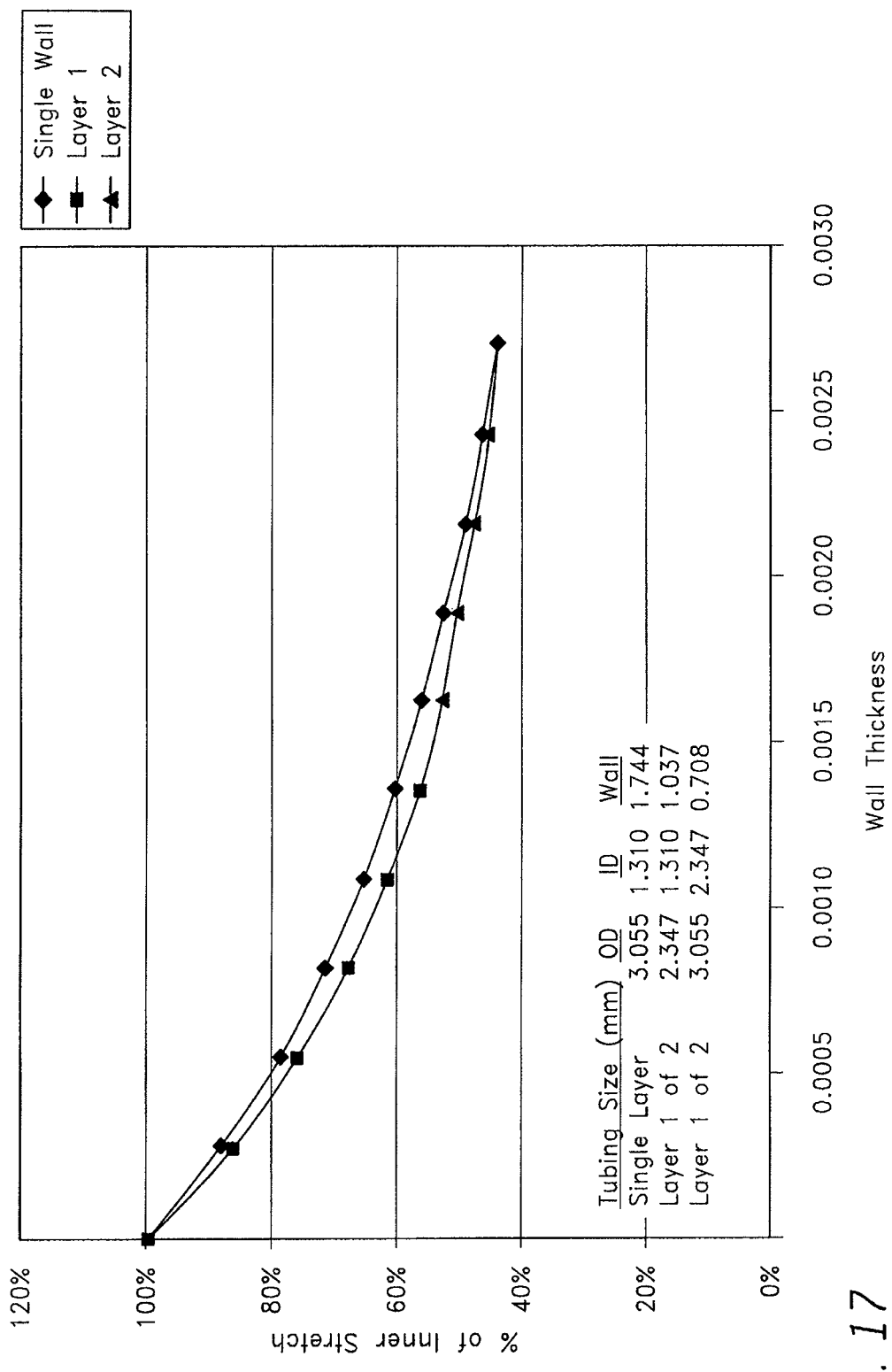
FIG. 17 is a graph of a single-layer balloon catheter and a two-layer balloon catheter manufactured from co-extruded tubing.

The problem of inner balloon bursting is particularly common for co-extruded multi-layer balloons because the interior balloon necessarily has a more optimized inner wall stretch compared to that of outer layers. This is shown in detail on FIG. 17, in which the relative stretch of the wall slices of a dual layer balloon made from co-extruded tubing is shown relative to a single wall balloon having the same overall wall thickness. Known methods of creating multi-layer balloons primarily focus on co-extruding balloon elements in order to create a multi-layer balloon. Known methods do not typically involve nesting balloons nor has the confounding effect of radial stretch been considered. Even so, in the case of nesting balloons, the interior balloon occasionally is made smaller to facilitate insertion into the exterior balloon, so the problem of varying stretching remains.

Figure 18:
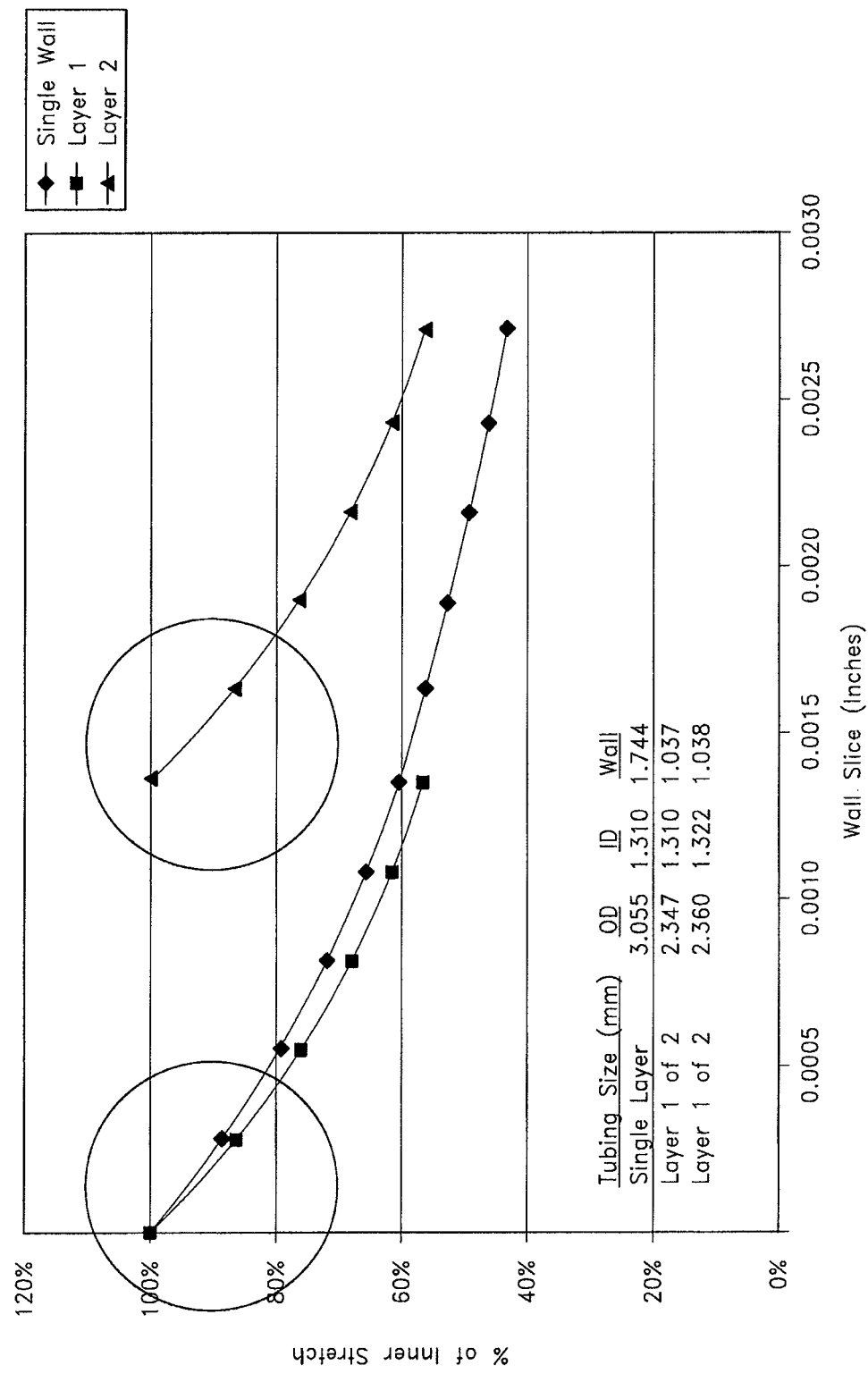
FIG. 18 is a graph of a single-layer balloon catheter and two-layer balloon catheter manufactured from tubing in which the inner wall stretch has been optimized for maximum strength.

In accordance with embodiments of the present invention, in order to substantially increase the overall wall strength of a multi-layer balloon, each balloon layer is molded from tubing in which the inner wall stretch has been optimized for maximum strength. FIG. 18 shows the relative stretch of wall slices for such a balloon having two layers. As can been seen, the relative amount of optimally stretched material is greater than that afforded by co-extrusion.

Using this design, it is not necessary that the layers be made from the same material or have the same wall thickness. Each layer is made such that the inner wall has been stretched for maximum strength, with the stretch ratio specific for that particular material. As described above, the inner wall should be stretched to within about 15% of its optimal stretch and, in some applications, preferably to within less than 10% of its optimal stretch. As the wall strengths are additive, the burst pressure will be higher than that for any individual layer. Once the burst pressure is reached, all layers will fail. The compliance characteristics for the layers will preferably be equivalent.

FIGS. 19A and 19B illustrate a balloon wall element 14 of a multi-layer balloon catheter 2. To maintain flexibility in each balloon layer 20, 22, 24, friction between these layers must be minimized. To illustrate this point we consider a balloon wall element 14. This element 14 has a thickness t equal to that of the balloon 2, or balloon layers 20, 22, 24, and a small width b and a length l. The element 14 can be configured either axially or radially. Taking one end of the element 14 as fixed, the element 14 can be viewed as a cantilevered beam for analytical purposes, as described below in FIGS. 20A through 20D.

Figure 20A:
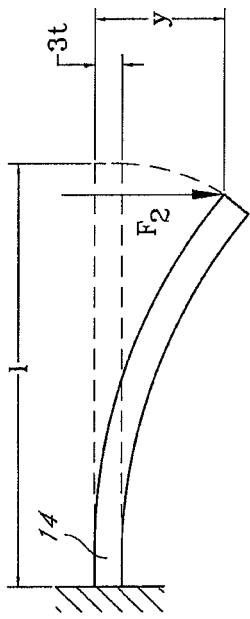
FIG. 20A is a diagram of a single layer element with a small thickness bending like a cantilevered beam shown with an applied force and a maximum deflection.
Figure 20B:
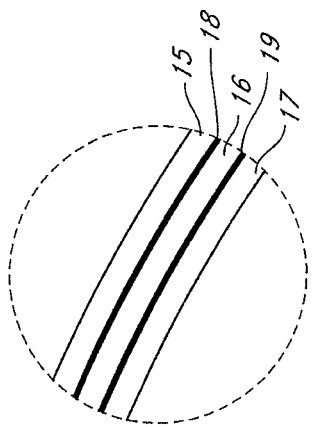
FIG. 20B is a diagram of a single layer element with a large thickness bending like a cantilevered beam shown with an applied force and a maximum deflection.
Figure 20C:
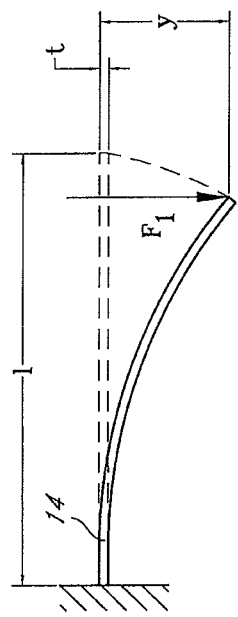
FIG. 20C is a diagram of a multi-layer element with three layers each having small thicknesses bending like a cantilevered beam shown with an applied force and a maximum deflection.

FIG. 20A shows the balloon element 14 as a single layer of thickness t. A balloon element 14 with thickness t requires a force $F_1$ to bend the element 14 a set distance y. FIG. 20B shows the balloon wall element 14 as a single layer of thickness $3t$. This thicker element 14 requires a force $F_2$, which is twenty-seven times larger than $F_1$, to bend the element 14 the same distance y as the element 14 in FIG. 20A (that is, because the force required varies as a cube of the element thickness). FIG. 20C shows a multi-layer element 14 comprised of a first element 15, a second element 16, and a third element 17. Each of the elements 15, 16, and 17 has an individual thickness t. As a result, the multi-layer balloon element 14 has a cumulative thickness $3t$. Each sub-element 15, 16, and 17 is individually as thick as the balloon element 14 in FIG. 20A, but collectively as thick as the balloon element 14 in FIG. 20B. Each individual element in FIG. 20C requires a force $F_1$ to bend a single balloon element a given distance y. Collectively, the multi-layer balloon element 14 requires a force $F_3$ to bend the element 14 a given distance y, which is three times as large as the force in FIG. 20A, but only one third as large as the force in FIG. 20B. As shown in FIG. 20C, each balloon element layer 15, 16, and 17 preferably slides relative to the other layers a distance Δl. If the balloon element layers 15, 16, and 17 are not permitted to slide, then the multi-layered balloon 14 will likely be equivalent to the equally thick balloon in FIG. 20B.

Figure 20D:
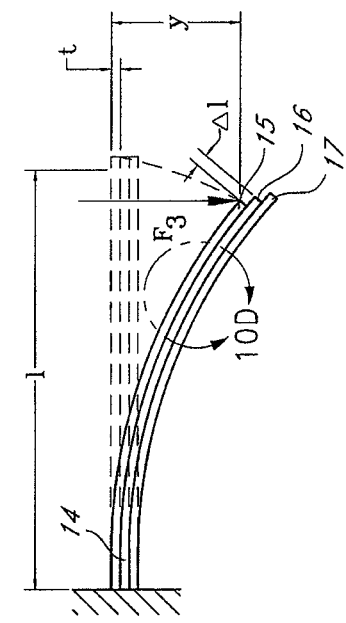
FIG. 20D is an enlarged side elevational view of the multi-layer element shown in FIG. 20C.

Referring now to FIG. 20D, because the layers 15, 16, and 17 are in close contact with each other and there is a potentially strong force pushing them together, frictional effects can be very significant and prevent sliding between the layers. To minimize friction between adjacent layers and to allow sliding, lubricating layers 18, 19 can be added in between structural layer 15, 16, and 17. The lubricating layers 18, 19 can be made of any suitable substance, nonexclusively including high density polyethylene, silicon oil, and carbon nanopowder, but in many medical applications should be biocompatible. It should be noted that lubricating layers are not necessary when friction between structural layers is allowable and, in some applications, desirable.

Figure 21:
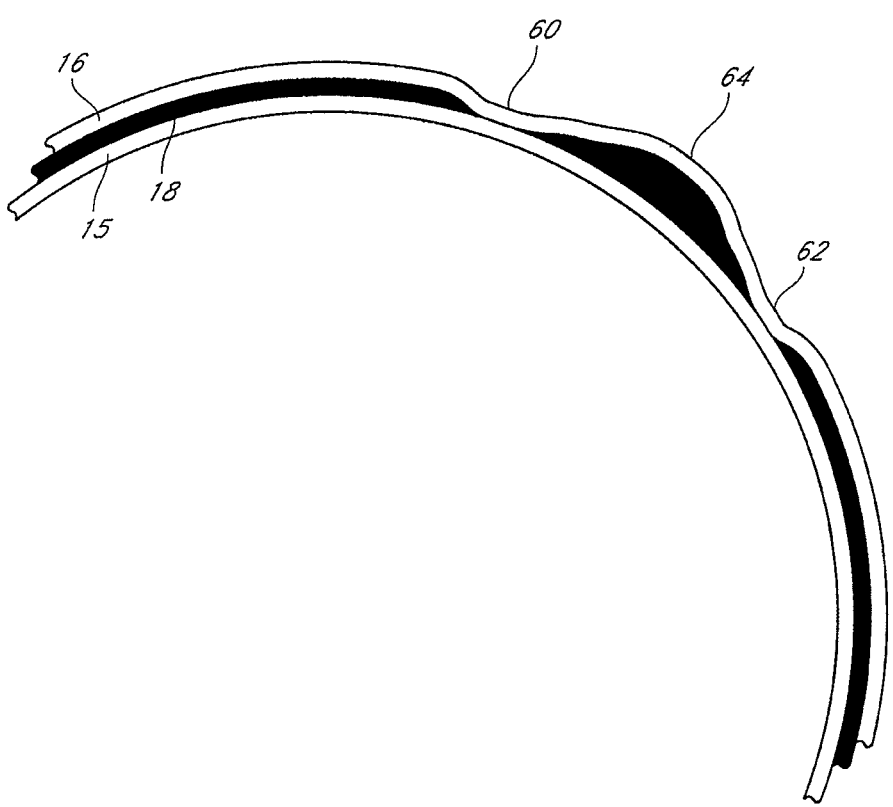
FIG. 21 is a cross-sectional view of a portion of a multi-layer balloon having a discontinuous lubricating layer.

With reference to FIG. 21, in some embodiments, lubricant should be distributed so as to substantially cover the entire surface area between adjacent balloon layers. The consequences of not having lubricant covering substantially the entire surface area are demonstrated in FIG. 21. Between adjacent balloon element layers 15, 16 there are two gaps 60, 62 shown in a lubricious layer 18. With the balloon inflated, this potentially creates substantial friction at the gaps 60, 62. Thus, an abnormally loose region 64 can form between the gaps 60, 62 with abnormally stretched regions adjacent the loose region 64. This unequal distribution of stress can cause a multi-layer balloon to burst prematurely. In some situations, spreading lubricant will be less of a concern. For example, low pressure applications and balloon regions with low stress may not require uniform spreading of a lubricious layer between adjacent balloon layers. It should be note that similar problems can develop between any two adjacent balloon layers if lubricant is not evenly distributed.

Embodiments of the multi-layer balloon disclosed herein can provide a significant performance improvement over current high pressure balloons. The disclosed embodiments allow for balloon catheters to be used in new applications. For example, multi-layer balloons can be used in ultra high pressure applications such as 50 atmospheres or more for up to 10 mm diameter balloons, and for high pressure applications for very large balloons such as 12 atmospheres or more for up to 30 mm diameter balloons. The advantages provided by the multi-layer balloons disclosed herein can be attributed, at least in part, to forming each layer from tubing where the inner wall stretch has been optimized for maximum strength.

Figure 22A:
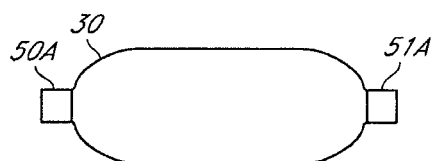
FIG. 22A is a side elevational view of an inner balloon used in a method for nesting balloons to form a multi-layer balloon.
Figure 22B:
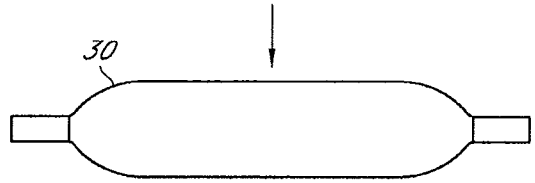
FIG. 22B is a side elevational view of the inner balloon after heating and stretching of the method for nesting multi-layer balloons of FIG. 22A.
Figure 22C:
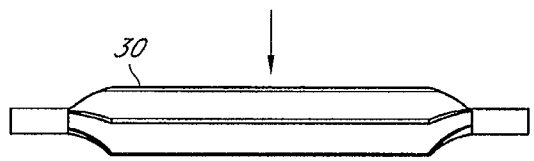
FIG. 22C is a side elevational view of the inner balloon after fluting of the method for nesting multi-layer balloons of FIG. 22A.

FIGS. 22A through 22G generally depict a method for nesting balloons to form a multi-layer balloon. As shown in FIG. 22A, an inner balloon 30 is provided having a proximal neck 50A and a distal neck 51A. The inner balloon 30 is then heated and stretched so that the diameter and cross-sectional area of the inner balloon 30 is decreased, while the length of the inner balloon 30 is at least partially increased, as shown in FIG. 22B. Heating and stretching the inner balloon 30 in this manner typically alters the alignment of the polymer molecules comprising the body of the balloon 30. The inner balloon 30 is then fluted using known fluting methods so that the balloon 30 comprises a plurality of flutes. The inner balloon 30 is then wrapped about a catheter shaft. The fluted and wrapped inner balloon 30 is illustrated in FIG. 22C. The balloon 30 can be fluted and wrapped, for example, using known fluting and wrapping machines. Embodiments of such machines can be found in U.S. patent application Ser. No. 11/303,546, filed Dec. 16, 2005 and entitled "Balloon Catheter Folding and Wrapping Devices and Methods," the contents of which are hereby incorporated by reference in their entirety. Other suitable balloon fluting and wrapping devices, however, can also be used.

Figure 22D:
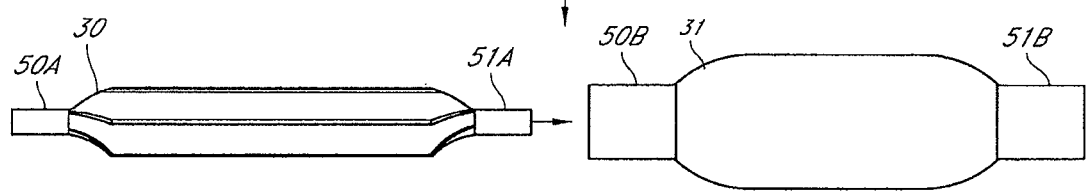
FIG. 22D is a side elevational view of the heated, stretched, and fluted inner balloon and an outer balloon used in the method for nesting multi-layer balloons of FIG. 22A.

With reference to FIG. 22D, the fluted and wrapped inner balloon 30 can be inserted into an outer balloon 31. The outer balloon 31 preferably has properties that are substantially similar, or in some cases identical, to those properties of the unstretched and unheated inner balloon 30 described with reference to FIG. 22A. In one embodiment, the balloons 30, 31 are comprised of tube stock that optimizes the inner wall stretch of the balloons 30, 31.

The outer balloon 31 has a proximal neck 50B and a distal neck 51B. In one embodiment, the proximal neck 50B and the distal neck 51B of the outer balloon 31 have larger diameters than the proximal neck 50A and distal neck 51A of the inner balloon 30. In one embodiment, the inner balloon 30 can be inserted into the outer balloon 31 by drawing it through the outer balloon 31 such that the inner balloon 30 is substantially contained within the outer balloon 31. Other suitable methods can also be used to insert the inner balloon 30 into the outer balloon 31.

In one embodiment of the present multi-layer balloon nesting method, the inner balloon 30 and the outer balloon 31 are blow-molded on the same mold (but preferably at separate times) so that the balloons 30, 31 have a substantially similar shape and size along a body portion of the balloons 30, 31. In this embodiment, the balloons 30, 31 preferably have proximal and distal necks having different sizes, as illustrated in FIGS. 22A and 22D. That is, the proximal and distal necks 50A, 51A of the inner balloon 30 have a smaller diameter than the proximal and distal necks 50B, 51B of the outer balloon 31.

Figure 22E:
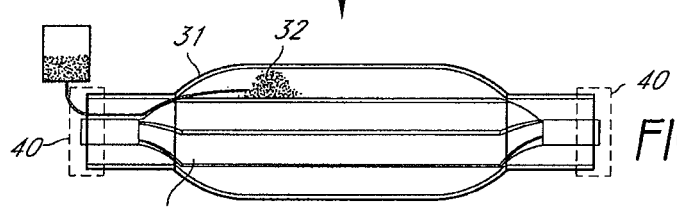
FIG. 22E is a side elevational view of a multi-layer balloon where lubrication is being applied between the inner balloon and the outer balloon of the method for nesting multi-layer balloons of FIG. 22D.

With reference to FIG. 22E, once the inner balloon 30 has been inserted into a cavity of the outer balloon 31, lubrication 32 can be added to a space disposed between the inner balloon 30 and the outer balloon 31. In one embodiment, the lubrication 32 comprises silicon oil. It should be noted that lubrication 32 can be added either before the insertion step shown in FIG. 22D, during the insertion step shown in FIG. 22D, or after the insertion step shown in FIG. 22D. In the illustrated balloon nesting method, as shown in FIG. 22E, lubrication 32 is added after the insertion step in FIG. 22D.

Figure 22F:
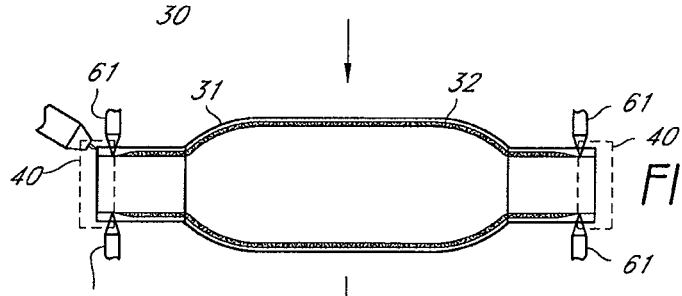
FIG. 22F is a side elevational view of the multi-layer balloon after heating, stretching, and inflating so that the inner balloon and the outer balloon have the same, or a substantially similar, degree of molecular alignment of the method for nesting multi-layer balloons of FIG. 22D.

As shown in FIG. 22F, the nested balloons 30, 31 are next heated, stretched, and inflated to bring the respective body portions of the inner balloon 30 and the outer balloon 31 into the same, or a substantially similar, molecular alignment. Embodiments of devices capable of inflating and heating a balloon can be found in U.S. patent application Ser. No. 11/303,545, filed Dec. 16, 2005 and entitled "Measurement Apparatus and Methods for Balloon Catheters," the contents of which are hereby incorporated by reference in its entirety. The embodiments presented can be modified to stretch the balloon as well, and also can be used to verify that the balloons have been stretched to an optimal size and shape. Other embodiments can be used to heat, stretch, and inflate the multi-layer balloons disclosed herein.

In one embodiment of the nesting method, one can heat and stretch the balloon and then begin inflating the balloon while continuing to heat and stretch the balloon. Inflation of the balloon can commence when approximately thirty percent of the stretching remains to be completed. The balloons are preferably stretched to four to five times their initial length. This amount of stretching is meant to optimize biaxial molecular alignment, and it will be apparent that a different method will be suitable for different applications.

With continued reference to FIG. 22F, a containing apparatus 61 can be used to prevent the lubrication 32 from reaching a welding zone 40. After sealing the balloons 30, 31, a lubricating layer 32 can be distributed evenly by mechanical means, if it is not sufficiently distributed during inflation.

Figure 22G:
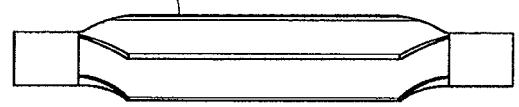
FIG. 22G is a side elevational view of the multi-layer balloon after fluting of the method for nesting multi-layer balloons of FIG. 22D.

As illustrated in FIG. 22G, the multi-layer balloon comprising the inner balloon 30 and the outer balloon 31 can be fluted and wrapped in preparation for attachment to a catheter shaft. In one embodiment, the multi-layer balloon is fluted and wrapped in preparation for insertion into another balloon. In another embodiment, the multi-layer balloon is fluted and wrapped in preparation for having another balloon inserted into a cavity defined by the multi-layer balloon.

The above-disclosed nesting method is particularly suitable for ultra high pressure balloons having large neck diameters relative to their body size. Further variations to the nesting method are possible such as, for example, repetition of this process to produce many-layered balloons, use of non-identically sized or shaped balloons, omission of lubricating layers for certain interfaces, and other suitable methods and processes.

The above-disclosed method comprising independent formation of an inner balloon and an outer balloon and then nesting the balloons allows for a variety of balloon sizes and shapes at each layer. Therefore, this method typically allows for ideal balloon parameters at each layer. However, in some instances, independent formation of balloon layers could be a slower and more costly process, particularly for balloons with small necks relative to their bodies. Typically, the body of the balloon is wider than its neck. However, the body of the inner balloon should still be capable of fitting through the neck of the outer balloon. The body of a balloon can be narrowed by heating, stretching, fluting, and wrapping. The neck of a balloon can possibly be widened by heating and inflating or stretching the balloon radially, but these methods are limited. As a result, it is often practical to form balloons independently and then nest them to create multi-layer balloons with a balloon body diameter to neck diameter ratio of 4 to 1 or less. For larger diameter-to-neck ratios, co-extrusion of some balloon layers might be preferable.

In the co-extrusion method, as discussed in further detail below with reference to FIGS. 23A through 23D, one avoids the difficulty of nesting balloons. However, the process of co-extrusion limits one's control over the size and shape of each balloon layer, potentially causing some of the problems discussed above, as well as others due to the general lost design freedom. In general, co-extrusion is more efficient than nesting in manufacturing larger multi-layer balloons, in the range above approximately 12 mm in diameter.

FIGS. 23A through 23D show one embodiment of forming multi-layer balloons using a co-extrusion method. As shown in FIG. 23A, a three layer balloon 26 and a two layer balloon 27 are provided. The three layer balloon 26 preferably has two structural layers 22, 24 and one lubricating layer 23. The two layer balloon 27 preferably has one structural layer 20 and one lubricating layer 21. In this embodiment, the three layer balloon 26 and the two layer balloon 27 are both co-extruded. In one embodiment, the structural layers comprise a polyamide such as Nylon 12. In one embodiment, the lubricating layers comprise 0.0001 to 0.00015 inch high-density polyethylene and/or carbon nano-powder filler.

With reference to FIG. 23B, the three layer balloon 26 is then processed to reduce its diameter and cross-sectional area in a manner similar to that disclosed above with respect to FIG. 22B of the nesting method. That is, the three layer balloon 26 can be heated and stretched so that the diameter and cross-sectional area of the three layer balloon 26 is decreased, while the length of the balloon 26 is at least partially increased. Heating and stretching the three layer balloon 26 in this manner typically alters the alignment of the molecules comprising the body of the balloon 26.

As shown in FIG. 23C, the three layer co-extruded and stretched balloon 26 (having a decreased diameter) can then be inserted into the two layer co-extruded balloon 27. In one embodiment, the three layer balloon 26 can simply be slid inside the two layer balloon 27. The lubricating layer 21 of the two layer balloon 27 (which can be disposed on an inner surface of the two layer balloon 27) facilitates relatively easy insertion of the three layer balloon 26 into the two layer balloon 27 because it reduces friction between the balloons when a structural layer 22 of the three layer balloon 26 (which can be disposed on an outer surface of the three layer balloon 26) contacts an inner surface of the two layer balloon 27.

With reference to FIG. 23D, the newly-formed five layer multi-layer balloon 25 can be heated, stretched, and inflated such that the inner balloon 26 alters its molecular orientation to an orientation that the inner balloon 26 had prior to the heating and stretching step of FIG. 23B (i.e., its original molecular orientation). As a result, the molecular orientation of the inner balloon 26 becomes substantially similar to, or the same as, the molecular orientation of the outer balloon 27 because these balloons had substantially similar, or the same, molecular orientations after co-extrusion (the step of FIG. 23A) and before drawing down the inner balloon 26 (the step of FIG. 23B).

Other variations of this co-extrusion method are possible such as, for example, repeating the method steps to create additional balloon layers, using additional co-extruded balloon layers, combining co-extrusion with balloon nesting, using alternative methods to achieve molecular alignment among the balloon layers, and other suitable variations. As discussed above with respect to the nesting method, in some embodiments of the co-extrusion method, it is important to have balloon layers comprising the substantially same size and comprised of materials having substantially similar mechanical properties.

Turning now to FIGS. 24A and 24B, before the multi-layer balloon is complete, the structural layers of the balloon are typically welded together. Unless the lubricating layers are to be welded as well, the lubricating layers preferably are kept away from a welding zone 40 of the multi-layer balloon. When a lubricating layer is not co-extruded, it can be injected relatively far from the welding zone and then mechanically dispersed, as shown and described above with respect to FIG. 22E. In FIGS. 24A and 24B, an analogous process is shown for a co-extruded lubricating layer 42 (as opposed to applying a lubricating layer in a nesting method for creating multi-layer balloons). In this embodiment, extrusion of the lubricating layer 42 is periodically halted to make a lubricating layer-free welding zone 40. In one embodiment, this is accomplished with a diverter valve. Use of the diverter valve can be adjusted to create a balloon parison of appropriate length. The structural layers 41, 43 of the multi-layer co-extruded balloon can then be welded together in welding zone 40. Other suitable variations can also be used to separate the lubricating layers from the welding zones.

FIGS. 25A through 25D show an embodiment of a method for forming two-layer balloons with each layer made from tubing that optimizes inner wall stretch for maximized balloon strength. As shown in FIG. 25A, a single-layer extrusion or tube stock 100 and a single-layer extrusion having a slip layer 110 are provided. The single-layer extrusion 100 preferably has a single, structural side wall 102. The single layer tube stock having a slip layer 110 preferably has a single, structural side wall 112 and a slip layer 114 disposed on the inner surface of the side wall 112. The tube stock with a slip layer 110 has a bonding zone 116 at each end of the tube stock 110. The bonding zone 116 defines an area of the tube stock 110 between the longitudinal ends of the side wall 112 and the ends of the slip layer 114. The bonding zone 116 provides an area free from lubrication, which allows the tube stock without a slip layer 100 to be bonded with the tube stock with a slip layer 110.

The single-layer tube stock 100 and the single-layer tube stock having a slip layer 110 are preferably formed from tubing that optimizes the inner wall stretch thus providing optimum balloon strength. In one embodiment, the extrusions 100, 110 may be formed from the same material and are preferably formed from the same, or a substantially similar, diameter of tube stock such that the degree of biaxial molecular orientation between the balloons 100, 110 is substantially similar. If the tube stocks 100, 110 are composed of the same material, then the diameters of the tube stock should be within about 10% of each other in order to provide balloon layers having a substantially similar degree of biaxial molecular orientation.

In one embodiment, the side walls 102, 112 comprise a polyamide such as Nylon 12. In one embodiment, the slip layer 114 comprises a layer composed of 0.0001 to 0.00015 inch high-density polyethylene and/or carbon nanopowder filler (i.e., "bucky balls" or graphite nanocarbon particles).

By way of example, for an 8 mm balloon made from Nylon 12, a tubing size of 0.090 inches by 0.056 inches may be used. The slip layer preferably will, at a minimum, cover a substantial portion of the main body of the balloon comprising the cylindrical portion of the balloon. However, in some applications, the slip layer may extend beyond the body of the balloon to cover at least a portion of the conical section of the balloon.

With reference to FIG. 25B, the single-layer extrusion 100 is then processed to reduce its diameter and cross-sectional area in a manner similar to that disclosed above with respect to FIGS. 22B and 23B. That is, the single-layer tube stock 100 can be heated and stretched axially so that its diameter and cross-sectional area are at least partially decreased, while the length of the extrusion 100 is at least partially increased. Heating and axial stretching the single-layer extrusion 100 in this manner typically alters the axial alignment of the molecules comprising the body of the extrusion 100, but induces little or no change to the radial or circumferential alignment.

As shown in FIG. 25C, the single-layer tube stock 100 (having a decreased diameter) can then be inserted into the single-layer tube stock having a slip layer 110 (having its original, unaltered diameter). In one embodiment, the single-layer extrusion 100 can simply be slid concentrically inside the single-layer extrusion having a slip layer 110. The slip layer 114 of the single-layer tube stock 110 facilitates relatively easy insertion of the single-layer tube stock 100 into the single layer tube stock having a slip layer 110 because it reduces friction between the balloons when the side wall 102 of the single-layer extrusion 100 contacts an inner surface of the single-layer extrusion having a slip layer 110.

With reference to FIG. 25D, the newly-formed two-layer balloon stock or parison 120 can be heated, stretched, and inflated such that the inner tube stock 100 alters its molecular orientation to an orientation that the inner tube stock 100 had prior to the heating and stretching step of FIG. 25B (i.e., its original molecular orientation). As a result, the degree of biaxial molecular orientation of the inner tube stock 100 becomes substantially similar to, or the same as, the degree of biaxial molecular orientation of the outer tube stock 110 because these balloons had substantially similar, or the same, molecular orientations at the beginning of the above-described process (the step of FIG. 25A) and before drawing down the inner tube stock 100 (the step of FIG. 25B).

It should be noted that in some applications of the multi-layer balloons formed using the methods described herein, such as the two-layer parison as described with reference to FIGS. 25A through 25D, the multi-layer parison does not necessarily have lubricating or slip layers. For example, the two-layer parison 120 of FIGS. 25A through 25D can simply comprise two single-layer extrusions formed from a substantially similar sized tube stock without having a slip layer disposed between the two side walls of the two-layer balloon stock 120.

Experiment to Test Superiority of Bi-Layer Balloon with Maximized Radial Expansion An experiment was conducted to test the superiority of a bi-layer balloon with maximized radial expansion. The experiment was performed using the following three high pressure balloon designs: (1) a bi-layer balloon with both balloons having maximized radial expansion ("Balloon Design 1"); (2) a bi-layer balloon, produced from telescoping extrusion, with balloons having different expansion ratios ("Balloon Design 2"); and (3) a single layer balloon having a relatively thick wall ("Balloon Design 3"). Tests were conducted and utilized to provide statistical proof of certain characteristics of the three high pressure balloon designs, such as burst pressure, compliance, and fatigue testing.

The results of the experiment indicate that a bi-layer balloon with both balloons having maximized radial expansion (i.e., Balloon Design 1) has a 12% greater burst strength and can be subjected to 46% more fatigue cycles than a bi-layer balloon with balloons having different expansion ratios (i.e., Balloon Design 2). The results also demonstrate that a bi-layer balloon with both balloons having maximized radial expansion (i.e., Balloon Design 1) has a 14% greater burst strength and can be subjected to 68% more fatigue cycles than a single layer balloon having a thick wall (i.e., Balloon Design 3).

Purpose of the Experiment:
  Create and test multiple variations of plausible, high pressure, Nylon 12 balloon designs.
  Challenge the theory that two nested balloons with maximized expansion ratios is superior to nested balloons with different expansion ratios and thick single walled balloons.

Tools and Equipment:
  All burst, compliance, and fatigue testing were completed with the following machines:
    PT-3070 (Pressure Regulation): IA Asset 620
    Laser Measurement System: IA Asset 326
    Temperature Control System: IA Asset 519
  Wall Thickness Measurement Tool:
    Mitutoyo Blade Micrometer: IA Asset 173
  Balloon Blowing Equipment:
    Balloon Forming Machine: 2210H/110V
    Computerized Double End Stretcher: CJS-3X12/110V
    Center Mold: 316061-408
    Distal End Plug: 502155-35
    Proximal End Plug: 502155-34

Part Number and Description of the Balloons Used for Patent Testing:
  1. 511023 (Balloon Design 1): Multilayer balloon with both balloons having maximized radial expansion.
    a. Inner and outer balloon extrusion part number: 315284-08
    b. Inner and outer balloon extrusion dimensions: 0.090"×0.056"
  2. 316085-X1 (Balloon Design 2): Multilayer balloon created from nested extrusion.
    a. Inner extrusion part number: 315284-08
    b. Inner extrusion dimensions: 0.090"×0.056"
    c. Outer extrusion part number: 315284-X1
    d. Outer extrusion dimensions: 0.126"×0.092"
  3. 316085-X2 (Balloon Design 3): Thick, single layer balloon.
    a. Extrusion part number: 315284-X2
    b. Extrusion dimensions: 0.124"×0.056"
  4. 316085-X3: Multilayer balloon created from nested extrusion. The inner layer extrusion is the same part number as the outer and is drawn down through a hot die so the outer diameter is slightly smaller than the inner diameter of the original tubing size.
    a. Extrusion part number: 315284-08
    b. Extrusion dimensions: 0.090"×0.056"

Description of the Testing Requirements:
  1. Burst and Compliance Testing: 10 samples per balloon part number.
    While being submerged in 37° C. water, the balloon diameter is measured and recorded while being stepped in 2 ATM increments. The pressure is stepped and recorded until the balloon bursts. Compliance percentage, average burst, and minimum burst strength ("MBS") are calculated.
  2. Fatigue Testing: 10 samples per balloon part number.
    Once the different balloons have been burst tested, the least MBS calculated will be used for fatigue testing. Each balloon will undergo cycles from 0 to MBS until the balloon bursts. The number of cycles will be recorded and an average will be calculated.

Balloon Development Notes:
  1. Balloon part numbers 511023, 316085-X1, and 316085-X2 were formed using usual balloon blowing techniques.
  2. Balloon part number 316085-X3 was not able to be formed.
    To start the development, the necked down inner tubing was solely used to form the 8 mm balloon.
    The logic used was if the inner balloon was not able to be formed, the nested extrusion will also not be able to be formed.
    The extrusion was not able to expand to the walls of the mold due to an inner expansion ratio of approximately 14:1.

Results:

| Balloon Wall Thickness Measurements | | | |
|---|---|---|---|
| | 316085 & 316086 (Standard) | 316085-X1 (Telescoped tubing w/o necking) | 316085-X2 (Thick wall tubing) |
| | Double Wall Thickness Measurement (Inches) | | |
| Burst Sample Number | | | |
| 1 | 0.0062 | 0.0065 | 0.0068 |
| 2 | 0.0062 | 0.0063 | 0.0069 |
| 3 | 0.0064 | 0.0063 | 0.0067 |
| 4 | 0.0063 | 0.0068 | 0.0067 |
| 5 | 0.0064 | 0.0064 | 0.0069 |
| 6 | 0.0062 | 0.0070 | 0.0069 |
| 7 | 0.0063 | 0.0065 | 0.0068 |
| 8 | 0.0064 | 0.0065 | 0.0069 |
| 9 | 0.0064 | 0.0069 | 0.0068 |
| 10 | 0.0064 | 0.0063 | 0.0068 |
| Average Double Wall Thickness (In) | 0.0063 | 0.0066 | 0.0068 |
| St. Dev. | 0.0001 | 0.0003 | 0.0001 |
| % St. Dev. | 1.5% | 4.0% | 1.2% |
| Relative Difference | 0% | 3.6% | 7.9% |
| Fatigue Sample Number | | | |
| 1 | 0.0064 | 0.0066 | 0.0068 |
| 2 | 0.0064 | 0.0065 | 0.0067 |
| 3 | 0.0064 | 0.0065 | 0.0067 |
| 4 | 0.0063 | 0.0063 | 0.0068 |
| 5 | 0.0064 | 0.0068 | 0.0069 |
| 6 | 0.0063 | 0.0066 | 0.0069 |
| 7 | 0.0065 | 0.0067 | 0.0069 |
| 8 | 0.0064 | 0.0067 | 0.0069 |
| 9 | 0.0063 | 0.0068 | 0.0068 |
| 10 | 0.0064 | 0.0067 | 0.0068 |
| Average Double Wall Thickness (In) | 0.0064 | 0.0066 | 0.0068 |
| St. Dev. | 0.0001 | 0.0002 | 0.0001 |
| % St. Dev. | 1.0% | 2.3% | 1.2% |
| Relative Difference | 0% | 3.8% | 6.9% |

| Burst Testing | | | |
|---|---|---|---|
| Burst Sample Number | 316085 & 316086 (Standard) | 316085-X1 (Telescoped tubing w/o necking) | 316085-X2 (Thick wall tubing) |
| 1 | 40.04 | 39.46 | 36.09 |
| 2 | 41.38 | 40.03 | 35.94 |
| 3 | 40.27 | 37.85 | 36.08 |
| 4 | 42.19 | 36.22 | 35.94 |
| 5 | 42.21 | 34.03 | 37.37 |
| 6 | 40.03 | 37.89 | 35.94 |
| 7 | 43.76 | 38.12 | 36.14 |
| 8 | 40.03 | 37.4 | 36.76 |
| 9 | 44.34 | 34.04 | 37.85 |
| 10 | 42.75 | 37.78 | 35.94 |

-continued

| | | | |
|---|---|---|---|
| Average Burst (atm) | 41.70 | 37.28 | 36.41 |
| Relative Burst (atm) | Standard | 35.93 | 33.52 |
| St. Dev. | 1.609 | 2.005 | 0.690 |
| % St. Dev. | 3.9% | 5.4% | 1.9% |
| K-Factor | 5.203 | 5.203 | 5.203 |
| MBS = fatigue pressure | 33.33 | 26.85 | 32.81 |
| Relative MBS | 33.33 (Standard) | 25.87 | 30.22 |
| Minimum (atm) | 40.03 | 34.03 | 35.94 |
| Maximum (atm) | 44.34 | 40.03 | 37.85 |

Fatigue Testing

| Fatigue Sample (number of cycles at fail) | 316085 & 316086 (Nested Balloons) | 316085-X1 (Telescoped tubing w/o necking) | 316085-X2 (Thick wall tubing) |
|---|---|---|---|
| Fatigue Pressure (atm) | 27 | 27 | 27 |
| 1 | 45 | 41 | 20 |
| 2 | 71 | 37 | 32 |
| 3 | 53 | 57 | 25 |
| 4 | 134 | 64 | 28 |
| 5 | 150 | 48 | 13 |
| 6 | 101 | 67 | 24 |
| 7 | 81 | 38 | 30 |
| 8 | 82 | 47 | 32 |
| 9 | 42 | 32 | 32 |
| 10 | 119 | 41 | 45 |
| Average Cycle Number | 88 | 47 | 28 |
| Standard Deviation | 37 | 12 | 9 |
| % St. Dev. | 42.7% | 25.1% | 30.4% |
| Relative Average | 88 (Standard) | 49 | 30 |

Description of Balloon Failure:
511023:
12% higher burst and 46% more fatigue cycles than 316085-X1.
14% higher burst and 68% more fatigue cycles than 316085-X2.
The superiority of the nested balloons is due to both balloons having the identical inner and outer expansion ratios.
The stresses caused by inflation and deflation are the same for each balloon when both have the same inner and outer expansion ratios.
When the stresses are the same, the balloons will burst at the same time which ensures maximized burst strength.
316085-X1:
The lower burst strength and fatigue cycles of this balloon are due to the nested tubing having different expansion ratios.
The outer extrusion has a medium expansion ratio of 2.9:1 while the inner extrusion has 4.4:1.
Due to the expansion ratio difference, the balloon layers are undergoing different stresses while being inflated and deflated.
During the burst test, two distinctive "pops" can be heard. The first rupture is the inner balloon and the second rupture is the outer balloon.
Due to the outer balloons lower expansion ratio, it can withstand more pressure and fatigue cycles than the inner balloon.
Once the inner balloon bursts, the second balloon immediately ruptures because the pressure is no longer contained by two layers.
318085-X2:
The lower burst strength and fatigue cycles of the thick walled balloon are caused by the same concept of a balloon with nested tubing having different expansion ratios.
The outer expansion ratio is 2.6:1 while the inner expansion ratio is 5.75:1. The inner diameter has to expand approximately 2.2 times farther than the outer diameter.
During the burst and fatigue testing, the inner surface of the balloon begins to fracture before the outer surface. This is due to the inner surface reaching its maximum expansion while the outer surface proceeds to grow.
Once a fracture begins on the inner surface of the balloon, it quickly tears through the entire wall of the balloon causing premature bursts.

According to the results of the experiment as set forth above, it is concluded that a bi-layer balloon constructed with two balloons with the same expansion ratios (i.e., Balloon Design 1) proves to have superior burst strength and cycle fatigue resistance when compared to a bi-layer balloon with balloons having different expansion ratios (i.e., Balloon Design 2) and to a single layer balloon having a thick wall (i.e., Balloon Design 3).

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims.

What is claimed is:

1. A method of making a nested balloon comprising:
   selecting an inner balloon layer and an outer balloon layer, the inner balloon layer and the outer balloon layer comprising the same polymer material;
   providing a lubricant, wherein the lubricant is configured to be co-extruded onto one or more layers or between layers, applied to one or more layers, or injected between layers;
   blowing the inner balloon layer and the outer balloon layer separately to stretch the polymer material to align molecular chains along an inner wall of each balloon layer, wherein the inner balloon layer and the outer balloon layer have substantially the same shape and size along a body portion of the inner balloon layer and the outer balloon layer; and
   positioning the inner balloon layer within outer balloon layer to form a nested balloon, wherein the nested balloon is configured to be expanded axially and radially in use.

2. The method as in claim 1, wherein blowing is accomplished before positioning the inner balloon layer within the outer balloon layer.

3. The method as in claim 1, wherein the lubricant comprises oil.

4. The method as in claim 1, wherein the outer balloon layer comprises nylon.

5. The method as in claim 1, wherein the inner balloon layer comprises nylon.

6. The method as in claim 1, wherein the inner balloon layer and the outer balloon layer fail at approximately the same pressure when a pressure is applied to the nested balloon.

7. The method as in claim 1, wherein the inner balloon layer and the outer balloon layer are configured to withstand at least about 40 atmospheres of applied pressure.

8. The method as in claim 1, wherein the inner balloon layer and the outer balloon layer are configured to withstand at least about 50 atmospheres of applied pressure.

9. The method as in claim 1, wherein the inner balloon layer and the outer balloon layer have substantially the same inner diameter.

10. The method as in claim 1, wherein the inner balloon layer and the outer balloon layer have substantially the same outer diameter.

11. The method as in claim 1, wherein blowing the inner balloon layer and the outer balloon layer separately comprises blowing the inner balloon layer and an outer balloon layer on the same mold at separate times.

12. The method as in claim 1, wherein the inner balloon layer and the outer balloon layer comprise different necks.

13. A method of making a nested balloon comprising:
   selecting an inner layer and an outer layer, the inner layer and the outer layer comprising the same material;

expanding the inner layer to within approximately 15% of the optimal radial stretch of an inner surface of the inner layer;

separately expanding the outer layer to within approximately 15% of the optimal radial stretch of an inner surface of the outer layer, wherein the inner layer and the outer layer have substantially the same shape and size along a body portion of the inner layer and the outer layer after expanding the inner layer and the outer layer; and positioning the inner layer within outer layer to form a nested balloon.

14. The method as in claim 13, wherein the outer layer comprises nylon.

15. The method as in claim 13, wherein the inner layer comprises nylon.

16. The method as in claim 13, further comprising providing a lubricant, wherein the lubricant comprises oil.

17. A method of making a nested balloon comprising:
selecting an inner balloon and an outer balloon, each balloon comprising the same material;
providing a lubricant between the inner balloon and the outer bal loon;
independently forming each of the inner balloon and the outer balloon by blowing the inner balloon and the outer balloon separately;
after independently forming each of the inner balloon and outer balloon, positioning the inner balloon within the outer balloon to form a nested balloon;
wherein, after positioning, the inner balloon and the outer balloon are configured to expand axially and radially.

18. The method as in claim 17, wherein the outer balloon comprises nylon.

19. The method as in claim 17, wherein the inner balloon comprises nylon.

20. The method as in claim 17, wherein the lubricant comprises oil.

* * * * *

UNITED STATES PATENT AND TRADEMARK OFFICE
CERTIFICATE OF CORRECTION

PATENT NO. : 10,835,720 B2
APPLICATION NO. : 15/701839
DATED : November 17, 2020
INVENTOR(S) : Josef J. Stupecky et al.

Page 1 of 1

It is certified that error appears in the above-identified patent and that said Letters Patent is hereby corrected as shown below:

On the Title Page

On Page 3, Column 2, Item (56), Line 11, under U.S. Patent Documents, delete "Lnenaga" and insert --Inenaga--.

In the Specification

In Column 12, Line 1, delete "($R_0/2$)" and insert --($R_o/2$)--.

In Column 12, Line 16, delete "($S_L=L_B\ L_t$)" and insert --($S_L=L_B/L_t$)--.

In Column 13, Line 19, delete "length 1." and insert --length l.--.

In the Claims

In Column 24, Line 5, Claim 17, delete "bal loon;" and insert --balloon;--.

Signed and Sealed this
Sixth Day of April, 2021

Drew Hirshfeld
*Performing the Functions and Duties of the
Under Secretary of Commerce for Intellectual Property and
Director of the United States Patent and Trademark Office*